US012098956B2

(12) United States Patent
Harvill et al.

(10) Patent No.: US 12,098,956 B2
(45) Date of Patent: Sep. 24, 2024

(54) SYSTEM AND METHOD FOR CREATION OF TOPICAL AGENTS WITH IMPROVED IMAGE CAPTURE

(71) Applicant: Shiseido Company, Limited, Tokyo (JP)

(72) Inventors: Leslie Young Harvill, Half Moon Bay, CA (US); Shawn Arseneau, Spring, TX (US)

(73) Assignee: Shiseido Company, Limited, Tokyo (JP)

( * ) Notice: Subject to any disclaimer, the term of this patent is extended or adjusted under 35 U.S.C. 154(b) by 293 days.

(21) Appl. No.: 17/493,519

(22) Filed: Oct. 4, 2021

(65) Prior Publication Data

US 2022/0026276 A1 Jan. 27, 2022

Related U.S. Application Data

(63) Continuation of application No. PCT/IB2020/000271, filed on Apr. 3, 2020.
(Continued)

(51) Int. Cl.
*G01J 3/50* (2006.01)
*G01J 3/02* (2006.01)
(Continued)

(52) U.S. Cl.
CPC ............... *G01J 3/50* (2013.01); *G01J 3/0264* (2013.01); *G01J 3/0272* (2013.01);
(Continued)

(58) Field of Classification Search
CPC ......... G01J 3/50; G06V 10/60; G06V 10/141; G06V 40/161
See application file for complete search history.

(56) References Cited

U.S. PATENT DOCUMENTS 5,249,263 A 9/1993 Yanker
5,315,508 A 5/1994 Bain et al.
(Continued)

FOREIGN PATENT DOCUMENTS

CN 101112304 A 1/2008
CN 105209870 A 12/2015
(Continued)

OTHER PUBLICATIONS

Translation of Japanese Office Action, counterpart 2021-559441, Mar. 5, 2024 (4 pages).
(Continued)

*Primary Examiner* — Maurice C Smith
(74) *Attorney, Agent, or Firm* — Calderone McKay LLC

(57) ABSTRACT

A method is described including displaying a user's body portion image on an optical display of a device employed by the user. The device may include an image sensor and the body portion image may be sensed by the sensor. The method includes determining whether a position of the body portion image relative to the sensor is acceptable to allow for recording of the body portion image; determining whether a lighting environment associated with the sensor is acceptable to allow for recording of the body portion image; recording the image using the sensor to provide a recorded image having image data; processing the recorded image to determine lighting model data associated with the lighting environment; and determining reflectance and color characteristics associated with the body portion based on the recorded image and the lighting model data. In one embodiment the optical display has an illuminant and when the lighting environment is not acceptable for recording, the method instructs the user to modify the lighting environment so that illumination of the body portion is less than about 2% of the illumination provided by the illuminant, illuminates (Continued)

the body portion with constant white light using the illuminant and determines whether the illuminated body portion is positioned relative to the sensor to allow for recording of the body portion image by displaying an outline of the body portion on the optical display to position the body portion in view of the sensor. Processing of the image in this case may include direct computation to determine the lighting model.

15 Claims, 10 Drawing Sheets
(4 of 10 Drawing Sheet(s) Filed in Color)

Related U.S. Application Data

(60) Provisional application No. 62/951,970, filed on Dec. 20, 2019, provisional application No. 62/859,676, filed on Jun. 10, 2019, provisional application No. 62/831,667, filed on Apr. 9, 2019.

(51) Int. Cl.
*G06V 10/141* (2022.01)
*G06V 10/56* (2022.01)
*G06V 10/60* (2022.01)
*G06V 40/16* (2022.01)

(52) U.S. Cl.
CPC ............ *G06V 10/141* (2022.01); *G06V 10/56* (2022.01); *G06V 10/60* (2022.01); *G06V 40/161* (2022.01); *G06T 2207/30088* (2013.01)

(56) References Cited

U.S. PATENT DOCUMENTS

| | | |
|---|---|---|
| 5,622,692 A | 4/1997 | Rigg et al. |
| 5,648,915 A | 7/1997 | McKinney et al. |
| 6,177,093 B1 | 1/2001 | Lombardi et al. |
| 6,510,366 B1 | 1/2003 | Murray et al. |
| 6,666,216 B2 | 12/2003 | Bourjal |
| 6,761,697 B2 | 7/2004 | Rubinstenn et al. |
| 6,856,861 B2 | 2/2005 | Dirksing et al. |
| 6,985,230 B2 | 1/2006 | De Rigal et al. |
| 7,061,617 B2 | 6/2006 | Querleux et al. |
| 7,324,668 B2 | 1/2008 | Rubinstenn et al. |
| 7,337,127 B1 | 2/2008 | Smith et al. |
| 7,634,103 B2 | 12/2009 | Rubinstenn et al. |
| 8,265,351 B2 | 9/2012 | Aarabi |
| 8,564,778 B1 | 10/2013 | Igarashi |
| 8,593,634 B1 | 11/2013 | Igarashi |
| 8,620,038 B2 | 12/2013 | Aarabi |
| 8,660,319 B2 | 2/2014 | Aarabi |
| 8,693,768 B1 | 4/2014 | LaForgia |
| 8,695,610 B2 | 4/2014 | Samain et al. |
| 8,725,560 B2 | 5/2014 | Aarabi |
| 8,830,468 B2 | 9/2014 | Igarashi |
| 8,856,160 B2 | 10/2014 | Beaver et al. |
| 8,933,994 B2 | 1/2015 | Gross et al. |
| 9,007,588 B1 | 4/2015 | Igarashi |
| 9,058,765 B1 | 6/2015 | Mallick et al. |
| 9,064,279 B1 | 6/2015 | Tuan et al. |
| 9,064,344 B2 | 6/2015 | Smith |
| 9,118,876 B2 | 8/2015 | Felt |
| 9,122,918 B2 | 9/2015 | Howell et al. |
| 9,122,919 B2 | 9/2015 | Howell et al. |
| 9,275,400 B2 | 3/2016 | Aarabi |
| 9,330,298 B2 | 5/2016 | Imai |
| 9,427,187 B2 | 8/2016 | Gilbert |
| 9,442,494 B2 | 9/2016 | Igarashi |
| 9,442,973 B1 | 9/2016 | Tuan |
| 9,449,412 B1 | 9/2016 | Rogers et al. |
| 9,460,462 B1 | 10/2016 | Walker et al. |
| 9,519,927 B1 | 12/2016 | Tuan et al. |
| 9,639,974 B2 | 5/2017 | Smith et al. |
| 9,760,935 B2 | 9/2017 | Aarabi |
| 10,083,345 B2 | 9/2018 | Choe et al. |
| 10,321,748 B2 | 6/2019 | Howell et al. |
| 10,943,279 B2 | 3/2021 | Stewart et al. |
| 11,445,803 B2 | 9/2022 | Howell et al. |
| 2002/0049643 A1 | 4/2002 | Church |
| 2003/0069667 A1 | 4/2003 | Dirksing et al. |
| 2003/0149504 A1 | 8/2003 | Iwaki et al. |
| 2003/0215471 A1 | 11/2003 | Wilmott et al. |
| 2006/0210154 A1 | 9/2006 | Leveque et al. |
| 2007/0145126 A1 | 6/2007 | Erlank et al. |
| 2008/0053167 A1 | 3/2008 | Basche |
| 2009/0271295 A1 | 10/2009 | Hodge et al. |
| 2010/0068247 A1 | 3/2010 | Mou et al. |
| 2010/0081971 A1 | 4/2010 | Allison |
| 2010/0123801 A1 | 5/2010 | Son et al. |
| 2010/0245823 A1 | 9/2010 | Chhibber et al. |
| 2010/0329995 A1 | 12/2010 | Deeter |
| 2011/0134275 A1 | 6/2011 | Nguyen |
| 2011/0199204 A1 | 8/2011 | Dionis et al. |
| 2011/0211047 A1 | 9/2011 | Chhibber et al. |
| 2012/0027269 A1 | 2/2012 | Fidaleo et al. |
| 2012/0076932 A1 | 3/2012 | Buelow et al. |
| 2012/0188367 A1 | 7/2012 | Marcu |
| 2012/0216911 A1 | 8/2012 | Bartholomew et al. |
| 2012/0229828 A1 | 9/2012 | Gill |
| 2013/0128686 A1 | 5/2013 | Bartholomew et al. |
| 2013/0148902 A1 | 6/2013 | Hyde et al. |
| 2014/0081463 A1 | 3/2014 | Igarashi |
| 2014/0094964 A1 | 4/2014 | Bartholomew et al. |
| 2014/0267664 A1 | 9/2014 | Gross et al. |
| 2014/0267665 A1 | 9/2014 | Howell et al. |
| 2014/0267783 A1 | 9/2014 | Howell et al. |
| 2015/0055086 A1 | 2/2015 | Fonte |
| 2015/0085279 A1 | 3/2015 | Balooch et al. |
| 2015/0107678 A1 | 4/2015 | Igarashi |
| 2015/0145680 A1 | 5/2015 | Favier et al. |
| 2015/0339754 A1 | 11/2015 | Bloem |
| 2015/0339757 A1 | 11/2015 | Aarabi |
| 2015/0346976 A1 | 12/2015 | Karunamuni et al. |
| 2015/0366328 A1 | 12/2015 | Tamura et al. |
| 2016/0027087 A1 | 1/2016 | Ahmed |
| 2016/0107133 A1 | 4/2016 | Sugino et al. |
| 2016/0125228 A1 | 5/2016 | Son et al. |
| 2016/0125624 A1 | 5/2016 | Liu et al. |
| 2016/0135730 A1 | 5/2016 | Arai et al. |
| 2016/0174690 A1 | 6/2016 | Howell et al. |
| 2016/0316886 A1 | 11/2016 | Samain et al. |
| 2016/0357196 A1 | 12/2016 | Igarashi |
| 2017/0011711 A1 | 1/2017 | Campbell et al. |
| 2017/0020436 A1 | 1/2017 | Flament |
| 2017/0178220 A1 | 6/2017 | Chong et al. |
| 2017/0228892 A1 | 8/2017 | Nichol et al. |
| 2017/0262920 A1 | 9/2017 | Hodge et al. |
| 2018/0260871 A1 | 9/2018 | Harvill et al. |
| 2019/0350345 A1 | 11/2019 | Howell et al. |
| 2020/0020011 A1 | 1/2020 | Harvill |
| 2021/0142382 A1 | 5/2021 | Stewart et al. |
| 2022/0026276 A1 | 1/2022 | Harvill et al. |

FOREIGN PATENT DOCUMENTS

| | | |
|---|---|---|
| EP | 1 196 893 B1 | 9/2003 |
| EP | 1 433 418 A | 6/2004 |
| EP | 1 488 737 B1 | 4/2010 |
| EP | 2 131 697 B1 | 9/2012 |
| JP | 2002-094868 A | 3/2002 |
| JP | 2002-131135 A | 5/2002 |
| JP | 2006-106951 A | 4/2006 |
| JP | 2006-254309 A | 9/2006 |
| JP | 2010-086036 A | 4/2010 |
| JP | 2012-128597 A | 7/2012 |
| JP | 2016-523574 A | 8/2016 |
| WO | WO 2001/091600 A2 | 12/2001 |
| WO | WO 2002/008983 A1 | 1/2002 |

(56) References Cited

FOREIGN PATENT DOCUMENTS

WO    WO 2014/114275 A1    9/2014
WO    WO 2015-126361 A1    8/2015

OTHER PUBLICATIONS

International Preliminary Examination Report, Counterpart Appln. PCT/IB2020/000271 (13 pages) Sep. 28, 2021.
Taiwan Office Action, counterpart 109111961 and English Translation, Dec. 12, 2023 (17 pages).
Chinese Office Action, counterpart 2020800401890 and English Translation, Jan. 31, 2024 (16 pages).
Japanese Office Action, counterpart 2021-559441, Mar. 5, 2024 (4 pages).
B. T. Phong, "Illumination for Computer Generated Pictures," Association for Computing Machinery, Inc. (1975), pp. 311-317.
S. Boivin et al., "Inverse Rendering from a Single Image," Dynamic Graphics Projects, University of Toronto, Canada and Mirages Project, INRIA-Rocquencourt, France, (8 pages) 2022 www.dgp.toronto.edu/~boivin/pubs/cgiv2002.pdf.
A. Alhakamy, "Real-Time Illumination and Visual Coherence for Photorealistic Augmented/Mixed Reality," ACM Comput. Survey 1, 1, Article 1 (Jan. 2020), 35 pages, https://doi.org/10.1145/3386496.
A. Chardon et al., "Skin Colour Typology and Suntanning Pathways," International Journal of Cosmetic Science 13, (1991) pp. 191-208.
S. Matsui et al., "Genetic Algorithm Can Optimize Hierarchical Menus," CHI 2008 Proceedings—Menu and Command Selection (Apr. 5-10, 2008—Florence Italy), pp. 1385-1388.
C. Donner et al., "A Layered, Heterogeneous Reflectance Model for Acquiring and Rendering Human Skin," ACM Transactions on Graphics, vol. 27, No. 5, Art. 140 (Dec. 2008), p. 140:1-140:12.
C. Donner et al., "A Spectral Shading Model for Human Skin," University of California, San Diego (no date).
I. Jang et al., "Makeup Color Reproduction Based on Spectrum Data," $19^{th}$ Korea-Japan Joint Workshop on Frontiers of Computer Vision, 978-1-4673-5621-2/13 (2013 IEEE), pp. 233-236.
G. Jalal, "Color Portraits: From Color Picking to Interacting with Color," Interacting with GUIs, CHI 2015, Crossings, Seoul, Korea, (Apr. 18-23, 2015) pp. 4207-4216.
J. Koenderink et al., "Color Picking: The Initial 20s", ACM Transactions on Perception, vol. 13, No. 3, Article 13 (Apr. 2016), pp. 13:1 to 13:25.
Barng, Keejung. "Makeup Design and the Application of 3D Facial Avatar Makeup Simulation." Journal of Fashion Business 18.6 (2014): pp. 57-66. (Year: 2014).
T. Chen, "Hyperspectral Modeling of Skin Appearance," ACM Transactions on Graphics, vo. 34, No. 3, Article 31, (Apr. 2015) pp. 31:1-31:14.
Li et al., "Simulating Makeup Through Physics-based Manipulation of Intrinsic Image Layers", Proceedings of the IEEE Conference on Computer Vision . . . (Year 2015).
B. Baumgart, "Winged Edge Polyhedron Representation," Stanford University, Advanced Research Projects Agency (1972), 44 pages.
T. DeRose et al., "Subdivision Surfaces in Character Animation," Pixar Animation Studios, (SIGGRAPH '98) 10 pages.
I. Jang et al., Makeup Color Reproduction Based on Spectrum Data, The $19^{th}$ Korea-Japan Joint Worksho on Frontiers of Computer Vision (2013), pp. 233-236.

SYSTEM AND METHOD FOR CREATION OF TOPICAL AGENTS WITH IMPROVED IMAGE CAPTURE

CROSS-REFERENCE TO RELATED APPLICATIONS

This application claims priority under 35 U.S.C. § 120 and/or § 119(a)-(d) to International Patent Application No. PCT/IB2020/000271, filed Apr. 3, 2020 and published in the English language as WO 2020/208421 A1, entitled "System and Method for Creation of Topical Agents with Improved Image Capture," and further claims the benefit under 35 U.S.C. § 119(e) of U.S. Provisional Patent Applications Nos. 62/831,667, filed Apr. 9, 2019, 62/859,676, filed Jun. 10, 2019 and 62/951,970, filed Dec. 10, 2019, each of which is entitled, "System and Method For Creation Of Topical Agents With Improved Image Capture," the entire disclosures of each of the foregoing applications of which are incorporated herein by reference.

BACKGROUND OF THE INVENTION

Field of the Invention

The field of the invention relates generally to image analysis and topical agent formulation and, more specifically, to systems and methods for determining a customized or select cosmetic formulation based on color facial images, using improved image capture techniques.

Description of Related Art

There has existed a need in the art for ways to provide custom or select topical agents, e.g., cosmetics, based on a determination of an individual's specific needs using, for example, advanced image analysis techniques. Systems and methods were thus developed to address these issues and allow a user to capture accurate, repeatable color samples using a mobile device. Methods to create a formulation for an aesthetic and protective topical agent optimized for a specific user and to provide the resulting product to the user were developed by the applicant herein and are disclosed in U.S. Pat. Nos. 8,933,994, 9,122,918 and 9,122,919 and/or U.S. Patent Application Publications Nos. 2018/0189853 A1 and 2018/0260871 A1 ("Background Patents"), each of which is incorporated herein by reference in relevant part. The implementation of these and other systems are now being used in industry, and are available in the marketplace. Companies such as MATCHCo. provide a full-stack solution to produce such agents. The systems and methods disclosed in these patents have many benefits, not only in enabling the practical production of these aesthetic agents, but in the ability of such systems and methods to characterize a given user's characteristics and use these characteristics to derive or recommend a user-specific cosmetic formulation and to provided modified cosmetic formulations based on an initial formulation through user interaction and feedback. Thus, a new formulation can be particularly formulated, selected and/or modified, based on such systems for an individual user.

Systems such as those described in the Background Patents disclose techniques to interactively guide a user to capture images and process the user interactions and resulting images using a device having an image sensor, which may be a hand-held device such as a mobile phone, for measuring facial regions, which result in determination, and ultimate manufacture, of a custom topical agent, such as a cosmetic. However, the user performance requirements, including user interaction time, associated with such techniques may be relatively high. For example, some previous methods required sequential collection of data from a plurality of facial regions to calibrate the device sensor for obtaining the most accurate image data. These performance requirements may result in lower adoption by end-users. Thus, there is a need for optimized methods for interactive capture of image data.

There are several existing approaches for capturing user optical data for a plurality of facial regions at the same time (i.e., in a single image capture). The simplest method for capturing optical image data of a user is for a user to take their own self-portrait or "selfie" image. This image data may be enhanced by machine vision services commonly available on operating systems for hand-held devices with cameras and interactive displays. Further, such image data may be augmented by the collection of three-dimensional (3D) surface data. It is increasingly common for machine vision services available on operating systems for hand-held devices to be augmented by optical systems which record 3D surface data. Still further, it is common for existing devices to provide services for tracking specific areas of a user's face, called facial landmarks. These landmarks may be related to, mapped upon, or used to generate a 3D surface by methods well-known to a practitioner of the art.

However, while use of a selfie is known, there is still a need in the art to improve the calibration and optical and camera data collection process and the resulting color accuracy to take account of the influence of environmental sources of light that can interfere with an accurate and calibrated image.

BRIEF SUMMARY OF THE INVENTION

The invention includes a number of embodiments that are directed to improving calibration and the optical and camera data collection process and the resulting color accuracy, including also doing so to take into account the influence where applicable of environmental sources of light that can interfere with an accurate and calibrated image. Exemplary embodiments of the invention are summarized herein.

The invention includes in one embodiment a method comprising: displaying an image of a body portion of a user on an optical display of a device employed by the user, wherein the device comprises an image sensor and the image of the body portion of the user is sensed by the sensor; determining whether a position of the body portion image relative to the sensor is acceptable to allow for recording of the image of the body portion; determining whether a lighting environment associated with the sensor is acceptable to allow for recording of the image of the body portion; recording the image using the sensor to provide a recorded image having image data; processing the recorded image to determine lighting model data associated with the lighting environment; and determining reflectance and color characteristics associated with the body portion of the user based on the recorded image and the lighting model data.

In one embodiment of the method, determining whether the position of the body portion relative to the sensor is acceptable for recording the image of the body portion may comprise displaying a colored light on the optical display.

In a further embodiment of the method, determining whether the position of the body portion relative to the sensor is acceptable for recording the image of the body portion may comprise displaying a lighted outline of the body portion on the optical display.

Further the method may include that determining whether the position of the body portion relative to the sensor is acceptable for recording the image of the body portion may comprise actuating a tactile or an audible indicator on the device.

In another embodiment of the method, determining whether that the lighting environment is acceptable for recording the image of the body portion may comprise displaying a colored light on the optical display.

It is further included in one method herein that determining that the lighting environment is acceptable for recording the image of the body portion may comprise displaying a lighted outline of the body portion.

In another embodiment of the method, determining that the lighting environment is acceptable for recording the image of the body portion may comprise actuating a tactile or an audible indicator on the device.

Determining the lighting model in the method may comprise: measuring exposure data associated with the device; determining data describing a relationship between an illuminant on the device and an aperture of the image sensor; determining data describing a relationship between the lighting environment and the image sensor; and determining data describing a relationship between the image sensor, the illuminant and a surface of the body portion.

The method may also further comprise determining a customized cosmetic formulation based in part on the reflectance and color characteristics.

In a method herein, various processing of the recorded image may be used for different lighting environments. Exemplary embodiments include that the optical display may comprise an illuminant; wherein illumination of the body portion by the lighting environment may be less than about 2% of the illumination provided by the illuminant; and wherein processing the recorded image to determine the lighting model data may comprise direct computation. The optical display may comprise an illuminant; wherein illumination of the body portion by the lighting environment may be between about 2% and 10% of the illumination provided by the illuminant; and wherein processing the recorded image to determine the lighting model data may comprise performing image filtering. The optical display may comprise an illuminant; wherein illumination of the body portion by the lighting environment may be between about 10% and 25% of the illumination provided by the illuminant; and wherein processing the recorded image to determine the lighting model data may comprise performing a statistical estimate of bilateral symmetry. Further the optical display may comprise an illuminant; wherein illumination of the body portion by the lighting environment may be between about 25% and 40% of the illumination provided by the illuminant; and wherein processing the recorded image to determine the lighting model data may comprises employing a machine learning technique.

In a further embodiment, the optical display may comprise an illuminant; and wherein when it is determined that the lighting environment associated with the sensor is not acceptable for recording the representation of the body portion, the method may then further comprise: instructing the user to modify the lighting environment so that the illumination of the body portion is less than about 2% of the illumination provided by the illuminant; illuminating the body portion with constant white light using the illuminant; and determining whether the illuminated body portion is positioned relative to the sensor to allow for recording of the image of the body portion by displaying on the optical display an outline of the body portion of the user to position the body portion within view of the sensor; wherein processing the recorded image to determine the lighting model data comprises direct computation.

The invention includes also an embodiment of a system comprising: one or more processors and non-transitory memory; machine-readable instructions stored in the memory that, upon execution by the one or more processors, cause the system to carry out operations comprising: displaying an image of a body portion of a user on an optical display of a device employed by the user, wherein the device comprises an image sensor and the image of the body portion of the user is sensed by the sensor; determining whether a position of the body portion image relative to the sensor is acceptable to allow for recording of the image of the body portion; determining whether a lighting environment associated with the sensor is acceptable to allow for recording of the image of the body portion; recording the image using the sensor to provide a recorded image having image data; processing the recorded image to determine lighting model data associated with the lighting environment; and determining reflectance and color characteristics associated with the body portion of the user based on the recorded image and the lighting model data.

Further included herein is a method comprising: (a) illuminating a body portion of a user with light of known intensity and color using an illumination source associated with an optical display of a device; (b) displaying on the optical display a representation of the body portion, the body portion being sensed by an image sensor of the optical device, wherein the representation of the body portion comprises an outline associated with the body portion and wherein the representation allows the user to position the body portion within the optical display; (c) recording an image of the body portion sensed by the image sensor; (d) recording data describing properties of the optical display, including the known intensity and color of the illuminating light, and properties of the image sensor, including exposure settings of the image sensor; and (e) determining a surface color of the body portion based on data associated with the recorded image of the body portion; the data describing properties of the optical display; and the data describing the properties of the image sensor.

In one embodiment of the method, the method may further include determining a distance from the image sensor to the surface of the body portion, wherein the distance is further used to determine the surface color of the body portion. In another embodiment, determining the surface color of the body portion comprises comparing the data associated with the recorded image of the body portion with the data describing properties of the optical display and the data describing the properties of the image sensor. The method may also further comprise calibrating the illumination source and an exposure sensitivity of the image sensor using data from a recorded image of the illumination source as reflected in a mirror. In such embodiment, the surface color of the body portion may be determined by processing the distance from the image sensor to the surface of the body portion; the data associated with the recorded image of the body portion; the data describing properties of the optical display; and the data describing properties of the image sensor using a network of weighted functions.

A system is also included herein comprising one or more processors and non-transitory memory; machine-readable instructions stored in the memory that, upon execution by the one or more processors, cause the system to carry out operations comprising: (a) illuminating a body portion of a user with light of known intensity and color using an illumination source associated with an optical display of a device; (b) displaying on the optical display a representation of the body portion, the body portion being sensed by an image sensor of the optical device, wherein the representation of the body portion comprises an outline associated with the body portion and wherein the representation allows the user to position the body portion within the optical display; (c) recording an image of the body portion sensed by the image sensor; (d) recording data describing properties of the optical display, including the known intensity and color of the illuminating light, and properties of the image sensor, including exposure settings of the image sensor; and (e) determining a surface color of the body portion based on data associated with the recorded image of the body portion; the data describing properties of the optical display; and the data describing the properties of the image sensor.

Also included herein is a method comprising: displaying an image of a body portion of a user on an optical display of a device employed by the user, wherein the device comprises an image sensor and the image of the body portion of the user is sensed by the sensor; recording a first version and a second version of the image of the body portion using the sensor to provide associated recorded high dynamic range images, wherein the display illumination on the optical display of the device is set to white to record the first version of the image and wherein the display illumination on the optical display of the device is set to black to record the second version of the image; removing at least some of the illumination in the second version of the image from the first version of the image to create a third version of the image; processing data associated with the third version of the image to create a three dimensional model of the body portion, the three dimensional model being associated with a series of vertices, each of the vertices being associated with a color; correcting the color associated with each of the vertices to account for distance of the sensor to the body portion and an angle of the sensor to the body portion to determine corrected color vertices; and processing the corrected color vertices using a machine learning model to estimate color characteristics of the body portion.

The method, in some embodiments, may further comprise operating the image sensor in self-portrait mode using an application. The method may further comprise controlling settings of the device having the image sensor using the application. In an embodiment of the method, it may further comprise taking the first version of the image in a dark room lighting environment, and further also illuminating the optical display with white light.

The method may in some embodiments further comprise storing the third version of the image in facial data format. In the method, each vertex may comprise one or more of: a label associated with the vertex's location on the body portion, an RGB color taken from the third version of the image, a depth of the vertex taken from depth data of the image sensor; a spatial location of the vertex relative to the image sensor's viewpoint, and the projected normal position of the vertex relative to the image sensor's viewpoint. In one embodiment of this method, the method may further comprise a pre-processing step to correct color based on the type of the device using image data from the device.

In this method, the machine learning model may include a color correction learning model and the method further comprises correcting for the type of the device while training the complexion color model and including images from different types of devices, including the device with the image sensor, as training data in the complexion color model. The training data for use in the machine learning model may be smoothed and filtered prior to training the machine learning model.

In the method further, the machine learning model may be built and trained using training data from human subjects, wherein the training data includes one or more of: survey data, self-reported data from the human subjects, reference photographs of the human subjects along with a color chart, skin color data from the human subjects measured by a spectrophotometer in at least one facial region used as ground truth measurements, and facial image data from users. The at least one facial region is selected from a wrist, a forehead, a right cheek, a left cheek, a right jaw line, a left jaw line and a décolletage.

The training data in the method that is skin color data from the at least one facial region used for ground truth measurements may be combined using a component median method into a single CIELAB color, and the single CIELAB color of each facial region may then be used as an input to a machine learning model, with the output of the machine learning model being a unified color for a facial cosmetic.

Alternatively, the training data that is skin color data from the at least one facial region used for ground truth measurements in the method may be combined using a composite method in which the skin color data from the at least one region is subject to linear weighting across the at least one facial region to determine which of the at least one regions is a best match to a single CIELAB value for a skin color in a ground truth dataset. In the machine learning model, in this embodiment, a CIELAB vector for each of the at least one facial region is an input to the model and a ground truth color CIELAB single vector is the output. The linear weighting may be calculated as a result of multivariate linear regression with regularlization. The machine learning model may include a ground truth dataset having ground truth data captured in summer months and ground truth data captured in winter months.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings, like reference characters generally refer to the same parts throughout the different views. Further, the drawings are not necessarily to scale, with emphasis instead generally being placed upon illustrating the principles of the invention.

In the drawings:

FIG. 1 illustrates a rendering of detected facial landmarks;

FIG. 2 depicts an exemplary optical display with combined line display and illumination;

FIG. 3 depicts an exemplary optical display with feedback to the user indicating poor user positioning during a self-portrait scan;

FIG. 4 illustrates a depth map of facial regions;

FIG. 5 illustrates a rendering of the geometry of facial regions derived from facial landmark detection;

FIG. 6 depicts the subdivision geometry from a geometry frame with depth sampling;

FIG. 7 depicts plane samples of facial regions that can be used with a lighting model;

FIGS. 8A and 8C are flowcharts of steps of an exemplary method for employing the optimized image capture techniques of the present invention; and FIG. 8B is a high-level exemplary system architecture that may be used in connection with embodiments of the present invention.

DETAILED DESCRIPTION OF THE INVENTION

Figure 1:
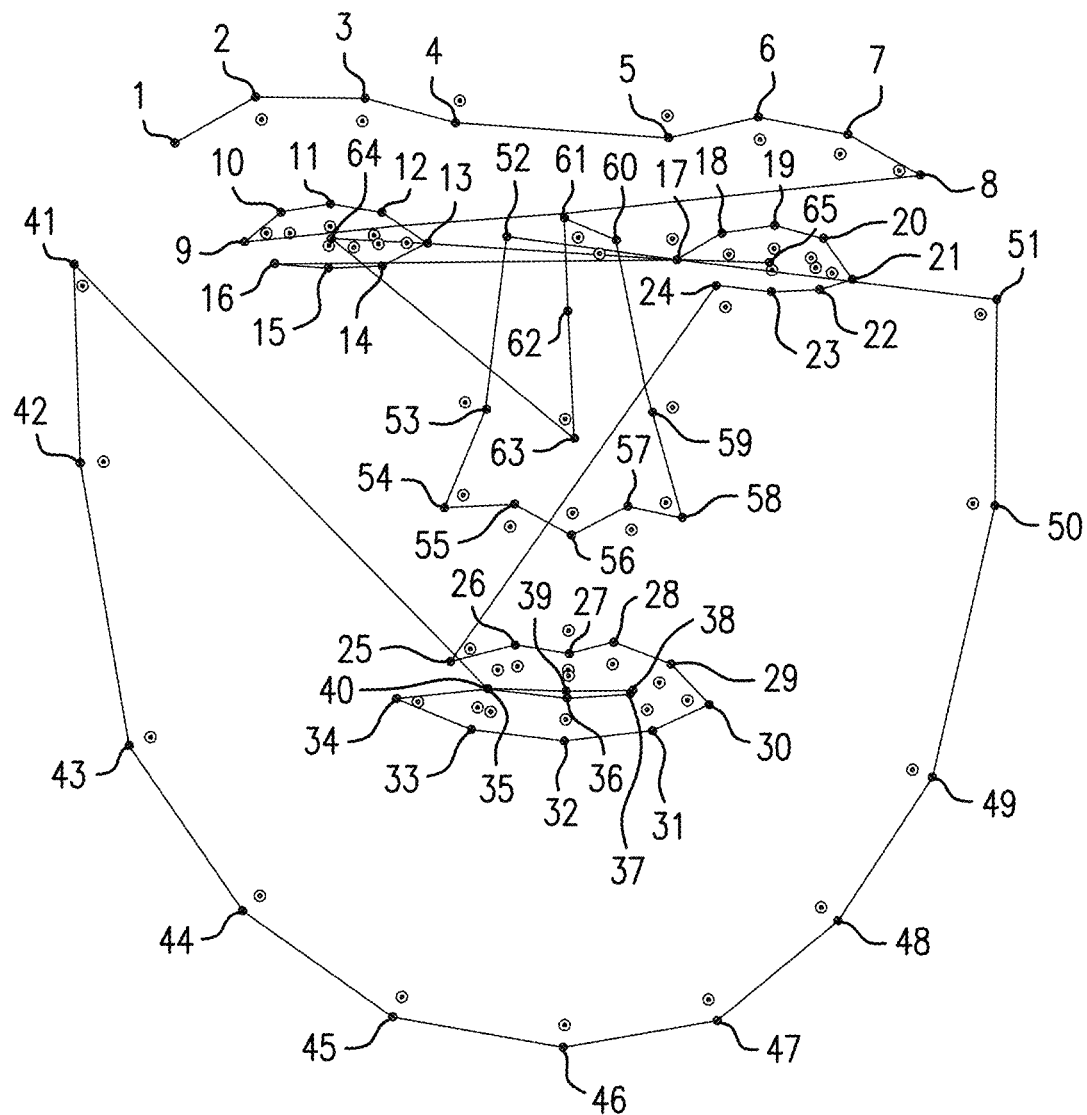

The following describes embodiments of the present invention and incorporates by reference in relevant part, as relates to the underlying systems and methods, the disclosures of the Background Patents to define the prior systems and methods therein which are useful to be employed in the present invention.

The invention and the embodiments thereof as described in this application provide an optical display (such as an illuminated liquid crystal display) for providing feedback to a user while serving also as a means of illuminating the user with a known amount of light for measurement of the complexion color of facial regions. The embodiments thus provide a form of controlled lighting, in addition to facial landmark tracking and facial surface reconstruction, to build a model of the unique lighting environment used for parallel optical data capture (i.e., in which several forms of optical data may be captured at one time). As used herein, the term "lighting model," or references to modeling a lighting environment, refer to a mathematical model of the physical propagation of light provided by an illuminating source, its interaction with physical surfaces, and subsequent sensing by an optical system. Such a model may be reduced to a practical application as data and code and used to provide information about image data.

Additionally, the captured data and the constructed lighting model can be used herein to train a machine learning system. Still further, the real-time captured data, the constructed lighting model may be processed by the trained machine learning system to provide detailed complexion color data (i.e., CIE 1*a*b*, CIELAB color), complexion feature data (e.g., wrinkles, freckles, acne, birthmarks), and to provide manufacturing instructions for interactive creation, modification and manufacturing of custom topical agents.

Embodiments of the invention disclosed herein also allow for the parallel collection of optical reflectance data from a plurality of facial regions of a user using optimized techniques, as described in more detail herein.

By way of background, the accurate recording (i.e., measurement and storage of data) of color using the sensor/camera of an optical device to record an image requires that the physical properties for sensor, lighting and the physical environment be controlled, known, or modeled.

As used herein, optical data refers to data captured by sensors and processed by an optical system of lenses to focus a real image onto an array of light sensing means, such as a charge coupled device (CCD). The output of the optical system is an image composed of color channels, or a greyscale channel. Optical data may include other data captured by optical systems including cameras and using other sensing methods. For instance, depth data may be sensed using an optical system that uses multiple cameras and timed or structured light output, such as is used in Time of Flight sensors and depth systems that use Structured Light.

Physical properties of the sensor are determined by reading embedded data in the optical stream, (e.g., optical data that may comprise a color image, depth data represented in an image array, as well camera settings, represented in exchangeable image file format (EXIF) or tag image file format (TIFF) formats, for example), or in the associated hardware through the operating system. Embedded data may include data in a data stream (e.g., a serial stream of data that is available in application programming interfaces (APIs) in the operating system (OS) of the device) composed primarily of raw or compressed image data which contains additional information about the data stream. Embedded data may include, but is not limited to, time of exposure used in image capture, aperture of a lens system used in image capture, sensitivity (ISO) of an image recording device used for image capture, location of the image capture in GPS coordinates, and make and model of the imaging equipment.

Lighting, as used herein, refers to sources of visible light, which can include local area light sources (such as lamps), diffuse area sources (such as light panels), and distance light sources (such as light from the sun and moon).

Physical environment, as used herein, refers to an indoor space (such as a room in a house or the interior of a car or vehicle) or an outdoor space including also the color and reflectance of surfaces in proximity to the activities performed in connection with image capture.

As described more fully herein, the relationship of the sensor, light, and surface reflectance of the target may be sensed and modeled using data supplied by 3D sensing functionality in the device/camera. Alternatively, the relationship may be sensed and modeled using technology that recognizes facial landmarks and fits these landmarks to the user's image (e.g., geometric data-fitting techniques using mathematical methods). Such technology may be supplied by computer vision algorithms in the operating system of the device, or other available sources, including open source projects such as STASM, OpenCV, or industry APIs such as Apple's ARKit, or Google's Vision API. Lighting and user interaction may be controlled using the device's optical display, as described more fully herein.

Embedded data that is exposure data of the optical sensor (i.e., ISO, shutter time, and aperture) may be obtained in several ways. In one exemplary embodiment, the exposure data embedded in the camera data stream is monitored to determine the exposure values of the sensor. In another embodiment, the system sets the shutter timing and the ISO sensitivity of the camera to specific settings. In either case, the amount of light in the scene may be measured using exposure data.

The relationship (i.e., the geometric relationship/placement relative to each other (6 degrees of freedom), position (xyz), orientation (yaw, pitch, roll or rotation about an axis)) between the illuminant (e.g., the "flash" or, while taking a self-portrait/selfie, the illumination from the optical display) and the camera may be determined by measuring the relative position and orientation of the illuminant and the aperture of the camera system. This data may be measured and stored in a data source for later use.

The relationship (i.e., geometric relationship, same as previous) between environmental illuminants and the camera also needs to be determined and may change depending on local lighting (lighting environment) and its corresponding radiosity mapping in the physical environment in relation to the camera aperture. For low light/dark room circumstances, determining the relationship between the position, orientation and subsequent contribution of environmental light to the camera may be as simple as detecting when the exposure information in the embedded image data indicates that such additional light is small in intensity. For circumstances in which the environmental illuminant is low, direct computation of the measured surface color may be simplified. A low illuminant environment is, e.g., one in which the total contribution of ambient or other environmental illumination sources is less than about 2% of the human perceivable luminance or color variance as measured by the CIELAB color found for the surface reflectance, where CIELAB is designed to be a close approximation of human perception of luminance and color using the Standard Observer model.

Such direct computation may be carried out by solving the radiosity equation, once the relative positions of the camera, skin surface, and light are known, and the amount of light is known (i.e., because there is no light source other than the display) and the exposure of the camera is known, the color of the skin may be solved as a physical system.

While the dark-room environment simplifies the overall process of solving for the lighting model (i.e., because having no external light removes the problem of solving for an unknown variable), other complications arise, as now described.

Many held-held devices contain camera systems and the ability to interact with the device using an optical display. Optical displays on hand-held devices continue to increase in quality of resolution, brightness, and color over time. The increase in the quality of brightness and color fidelity in these devices allows them to function as systems for illumination as well as for display. This use is well-known, and is often used by embedded software on the device to serve as a "flash" or fill light in the camera code interface. It is also common to show real-time output of the camera on such an optical display as feed-back to the user taking a selfie. However, during such real-time feedback, in a dark-room environment, it is not possible to use the display as an illuminant. This is because showing a video image on the display screen of someone in a dark room attenuates the light displayed on the screen. The light displayed on the screen, being dark, fails to illuminate the subject of the selfie. Lack of illumination in a dark room makes it difficult, if not impossible, to properly position the user's face for the selfie photograph.

Certain aspects of the present invention help to solve this problem. In one embodiment, the optical display is used for both feedback and as an illuminant in a dark-room environment, which involves indicating on the optical display that the image sensor is positioned such that the body portion that is the subject of the selfie scan may be detected automatically, e.g., using facial landmark detection techniques as described herein, and the optical display illuminates the body portion with greater luminous flux than other light sources. More particularly, the hand-held device can be programmed to show the user a representation of herself as an outline, line-drawing, or other sparse rendering (as described in more detail below) with constant/near-constant luminance on white background (such illumination coming from the illuminant display of the phone). Such a rendering may be accomplished in several ways. In one embodiment, an image processing algorithm used to find edges, such as Canny Edge Detection, may be used to find the edges of the face. These edges can be shown as light lines on a white background. This allows the device to give positioning feedback to the user while providing near-constant/continual illumination.

Figure 2:
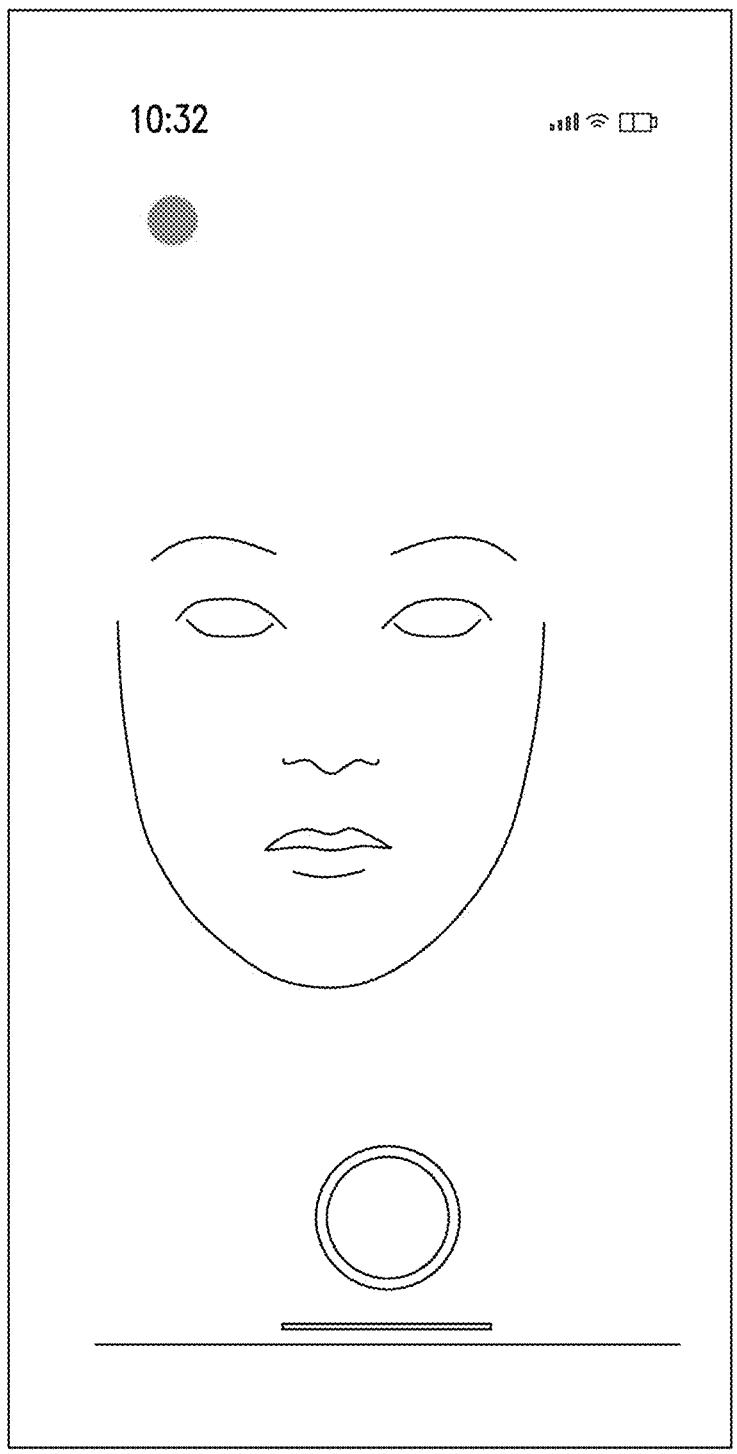

A method for creating a line-drawing/sparse rendering representation of the user's face is now described. A facial feature detection algorithm (e.g., provided by the machine vision services of the hand-held device operating system or facial feature detection APIs, as previously mentioned) may be used to locate key points of the user's face (as shown in FIG. 1). The software knows the points of the face. New points may be added by using proportional relationships to existing points. Then, the line drawing is created by connecting the dots. These points may be used to construct a light-yellow line drawing on a white background (as shown in FIG. 2), thereby allowing the system to give positioning feedback to the user while providing near-constant illumination. This rendering can show the position of the user in the frame so that she may properly position the self-portrait. In this manner, it is possible to use the optical display as both an illuminant and as feedback for positioning and alignment in a dark-room environment.

Additionally, in certain embodiments, mostly applicable where the room has at least some light, the rendering may vary to display when the user has positioned the camera at a near-optimum location and distance. The optimum user positioning may be determined by several factors. One factor is the distance of the user from the camera. For instance, at a very close distance, all needed features of the user may not be visible, the user's features may be out of focus, and/or the algorithm(s) used to locate facial landmarks may fail. If the user is too far from the camera, the number of pixels representing the user's features may be reduced so that data collection is impaired. If the user is not centered within the image area, key user features may be clipped. If the user's head is turned to the side, that orientation of the user may hide certain features.

In one embodiment, the rendering may be a line drawing describing the contours of the face when the phone is in the proper position and turn into an oval that encircles the face when it is not. More particularly, the facial feature detection software is able to detect the location of the facial landmarks to determine if the user's facial features are visible within the frame and acceptable for recording the image. If facial features are not all visible within the image frame, an oval is rendered.

Figure 3:
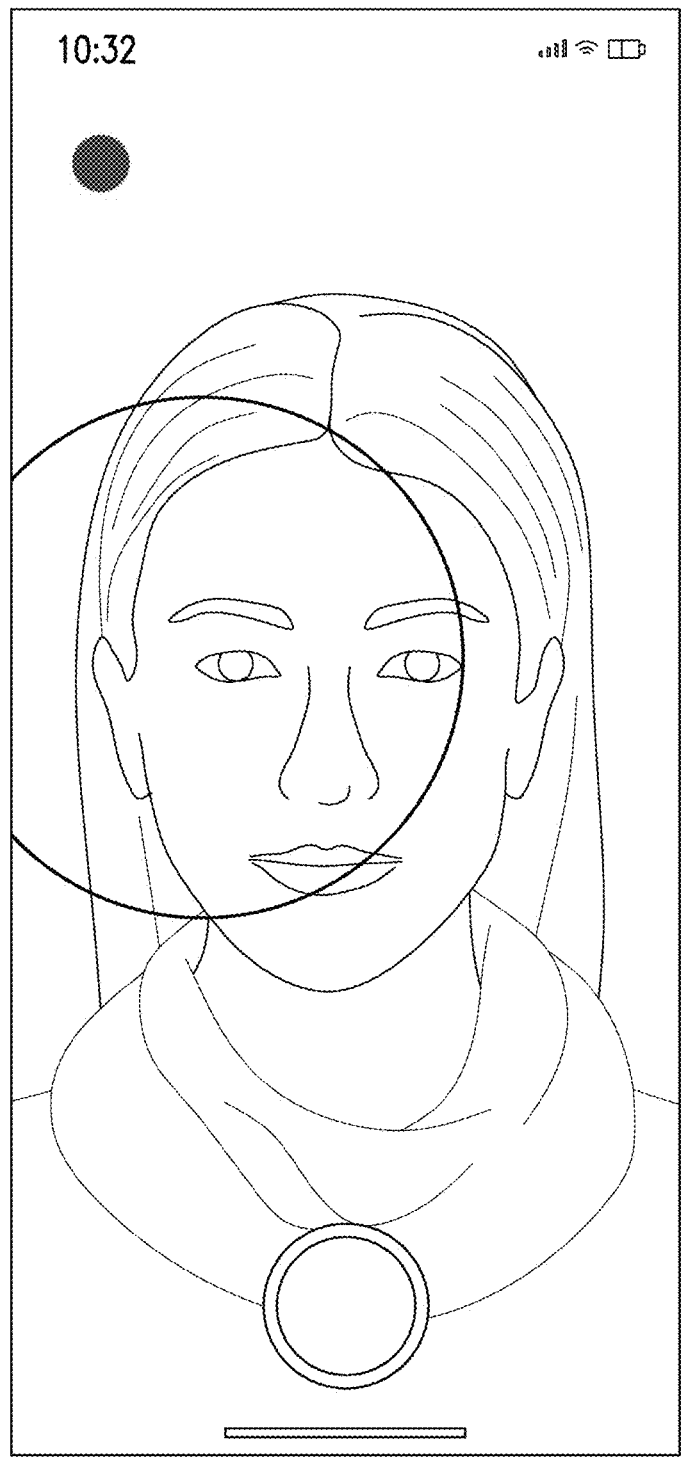

In another exemplary embodiment, the rendering may display pale linear edges of the face when the phone is in the proper position (as shown in FIG. 2) and turn into a low contrast bright video rendering of the user when it is not (as shown in FIG. 3). In some embodiments, the requirements for low ambient and environmental light are relaxed, and the entire lighting environment is solved using additional computation, employing Newton's method, as described in the following sections. However, even in such embodiments, providing user feedback by way of the optical display using the methods described in the preceding paragraphs is still useful, since direct illumination by the optical display may still be required, even for situations in which there is more ambient/environmental light.

For a lighted-room environment, to account for greater environmental light illumination, finding the relationship between the camera and environmental illuminant can be more complex. One exemplary solution involves capturing multiple images using multiple illuminants to adjust the calculated surface color. In this embodiment, an image is recorded by the user, using the method of taking a 'selfie' as described above with the color of the optical display being a known, calibrated white. In one embodiment, the screen color and brightness are measured for a given model of phone and used as a constant. In other embodiments, where the screen color and brightness for a given model of phone is too variable and cannot be considered constant, the white screen may be calibrated by having the user take a picture of herself in a mirror. That image can be used to calibrate the white screen of the phone—i.e., the white light in the image can be measured and, thus, become known. Techniques for embodiments of this step are described in one example in the Background Patents, as well as described further here. For example, in one exemplary embodiment, the user is directed by a series of user interface screens to show the display of the handheld device to a common mirror. The exposure settings of the camera/phone are set to known values. The user is asked to press a user interface element to record an image of the image of the screen with the front camera of the hand-held device. Software on the hand-held device uses the recorded image, the known exposure settings, the type of the hand-held device, and the size and recorded brightness of the bright display in the image to calibrate the illumination of the display and the exposure sensitivity of the camera. This calibration information may then be used to improve the calculation of complexion color by using the found display illumination brightness and color relative to the exposure characteristic of the camera to adjust the white point for color conversion.

Returning back now to the description of one method of accounting for environmental light illumination in the lighted-room environment, after the selfie has been taken, the color of the optical display illuminant is changed (e.g., to yellow) and the image is recorded. The color (e.g., yellow illuminated) image is used to detect those areas of the image where there is illuminated color of a different frequency (i.e., a color other than yellow). This information is used to remove environmental lighting from the first (i.e., white calibrated) image.

Describing this embodiment now in more detail, software on the hand-held device displays a series of separate background colors on the optical display, and an image is recorded for each separate illuminant. One of these illuminants may be the most intense yellow as defined by the sRGB standard (R=1, G=1, B=0). Another illuminant may be white as defined in the sRGB standard (R=1, G=1, B=1). Then, the following steps may be performed by the software to detect and remove ambient light: 1. Non-Yellow (blue) regions of the image of the user with the yellow illuminant are found. 2. These regions are processed to remove artifacts of exposure saturation, which is done by attenuating regions of high exposure. 3. These regions are processed to remove noise, which may be done by applying a median image filter. 4. These found regions are used to attenuate the exposure of the image of the user with the white illuminant. 5. The resulting corrected image may be used to refine subsequent calculation of surface color. Artifacts of exposure saturation, in this context, are very bright reflections that appear to be pure white in the recorded image. These may be detected by a histogram of the luminance, found and removed. Removing noise, in this context, may be performed by applying a component median filter of radius 1.0 to the captured image, using known techniques.

In the lighted-room environment, the hand-held device may be programmed to provide one indication that image data may be collected and another when it may not. For example, in one embodiment, when embedded exposure data read from the camera data stream indicates that the ambient light environment is too bright or otherwise is not acceptable for the optical display to be the main illuminant of the user, an indication may be made (e.g., is a red dot, as shown in the upper left hand corner of the display in FIG. 3), but when the embedded exposure indicates that the ambient light environment is dark enough for the optical display to be the main illuminant of the user, and the lighting environment is acceptable, a different indication may be made (e.g., is a green dot, as shown in the upper left hand corner of FIG. 2). In other embodiments, the indicator is not visual but audible or tactile.

Describing this embodiment now more particularly, ambient, environmental, and other light sources that are not the optical display may be considered "too bright" when their total contribution is greater than the contribution of the optical display, such that it is difficult for a software algorithm or method to accurately solve for the surface reflectance of the desired regions of the user's complexion. More or less light may be tolerable or acceptable depending on the techniques available to be used to account for such light—i.e., solving the lighting model directly is very sensitive to ambient light, while a machine learning system may be trained to ignore much more ambient light. For example, in embodiments in which reflectance is solved directly (e.g., by inverse rendering techniques, unaided by image filtering, additional statistical or machine learning techniques as described elsewhere herein), the required amount of illumination, other than that provided by the optical display, may be quite small. For instance, because this additional illumination will directly affect the tolerance of the found measure of the complexion color, it may be required that additional or ambient illumination falling on the complexion surface to be measured be less than about 2% of the illumination provided by the optical display (i.e., the amount of ambient light allowed from sources other than the display, as a percentage of the light output from the display as it strikes the skin).

In another embodiment, where ambient or other additional illumination may be attenuated by the image filtering described above, it may be required that additional or ambient illumination falling on the complexion surface to be measured be less than about 10% of the illumination provided by the optical display.

In yet another embodiment that adds a statistical technique that estimates the allowed variance of reflected light for areas of the face, and the statistical estimate of bilateral symmetry of reflectance of the face under known illumination, it may be required that additional or ambient illumination falling on the complexion surface to be measured be less than about 25% of the illumination provided by the optical display. For instance, since the light from the optical display is approximately centered, and the features of the face have been detected, it is useful to compare the illumination of regions of the face using bilateral symmetry (given that humans are roughly symmetrical, laterally). If there is a significant difference in the found reflected color for the right side of the face from the left, the difference may be used to detect external light on the brighter side of the face.

In a further embodiment that adjusts the output of the previous embodiments using a machine learning system trained by a wide range of possible complexion, lighting, and ambient inputs, it may be required that additional or ambient illumination falling on the complexion surface to be measured be less than about 40% of the illumination provided by the optical display. In these embodiments, the required restriction on additional or ambient illumination is tested and known, and the amount of additional illumination may be detected by monitoring the output of data embedded in the image data stream.

The physical relationship between the sensor, illuminant and target surface also needs to be determined (physical relationship, as previous). In one embodiment, the optical display (which is the illuminant in the self-portrait/selfie mode of operation) is in a fixed position relative to the optical sensor/camera. The system can determine the type of device it is operating and use this relationship (i.e., the physical distance and orientation of the display relative to the camera, which will not change for a given model of phone) to determine the physical relationship of the sensor/camera to the illuminant. In order to determine the relationship of the sensor and illuminant with the target surface, the various depths of the target surface must be determined. In one embodiment, the hand-held device (e.g., smart phone) has a sensor which measures depth as an array.

Figure 4:
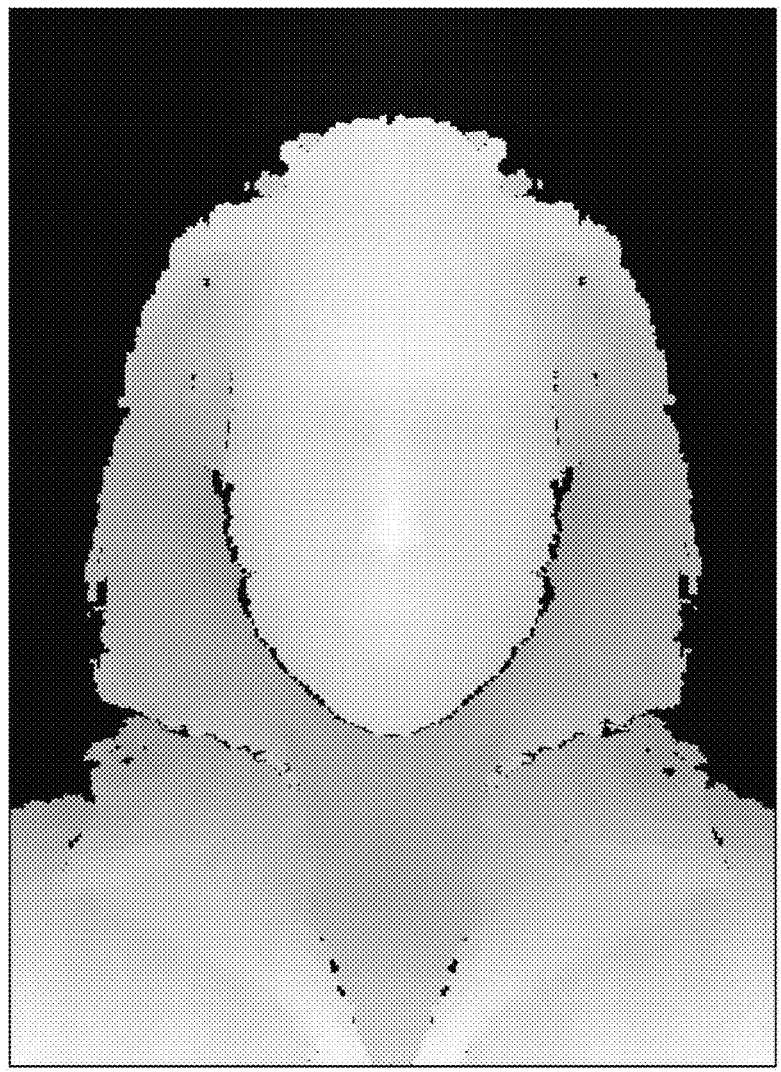
Figure 5:
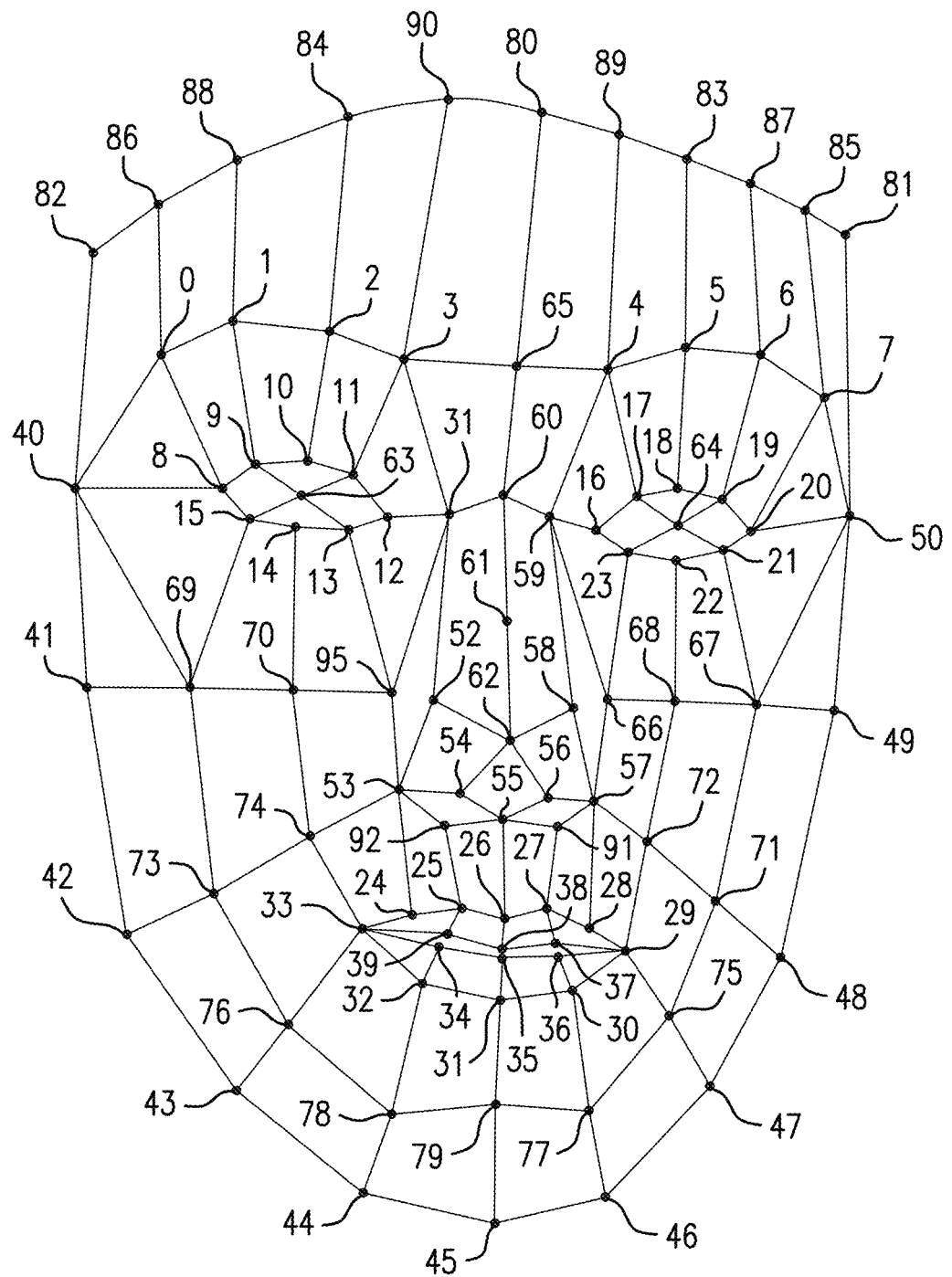
Figure 6:
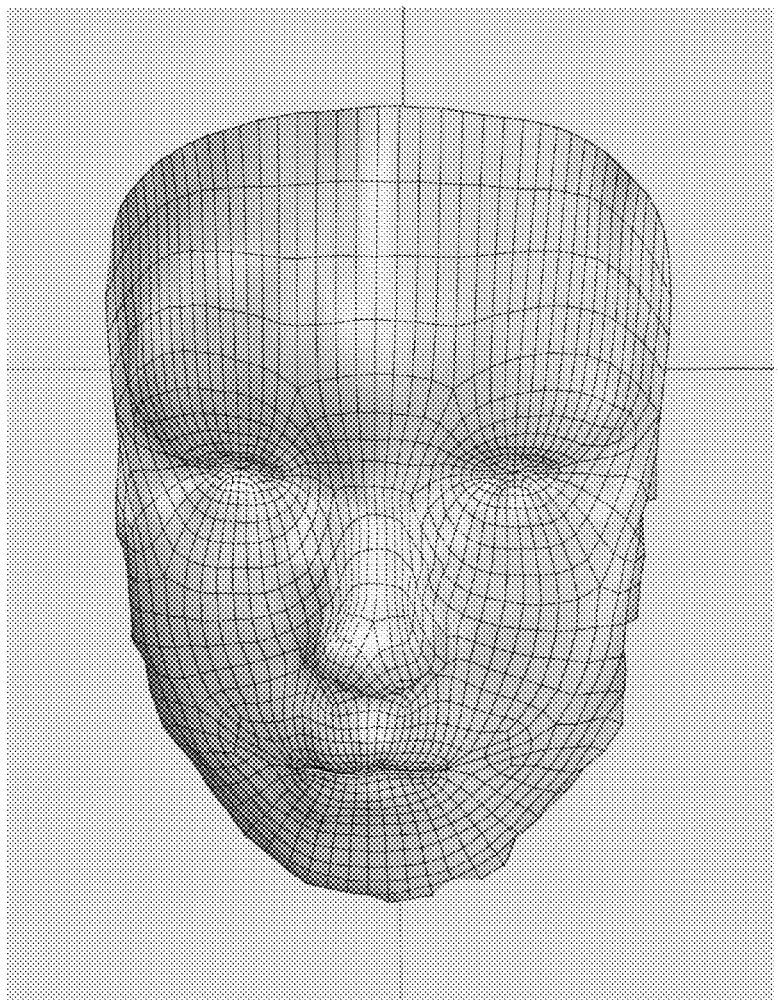

FIG. 4 shows the depth output of such an array as a grey-scale image. In FIG. 4, lighter areas are closer to the camera aperture, and darker areas are further away. It may be appreciated that each tone of grey represents a fixed, calibrated distance from the camera aperture, and so may be used to construct a 3D surface related to the optical image. In this manner, the relationship of the target surface to the camera is determined. In another embodiment, a machine-vision technique is used to find facial landmarks on the image (e.g., using APIs as previously mentioned). FIG. 1 shows the two-dimensional (2D) points that are output from a hand-held device using a service in the operating system for facial feature landmark tracking. The points are linked by a line in their array order. FIG. 5 shows the points in FIG. 1 augmented using a fitting algorithm to build a graph of nodes and arcs to form a set of connected 3D polytopes. The data structure used to hold this graph is called a Winged-Edge model. The fitting algorithm used in this example uses found facial landmarks to determine new positions for a pre-made graph, the positions being found by a system using replacement, scaling, interpolation and extrapolation. There are known algorithms that can be used to perform such a fit. For instance, Singular Value Decomposition may be used to build homogeneous projection matrices for a subset of landmarks, and these matrices may be used to map sections of the Winged-Edge model to the landmark positions. A depth map, such as illustrated by FIG. 4, may be used to apply sensed depth positions to the transformed Winged-Edge Model. FIG. 6 shows a Winged-Edge model that has been smoothed using selective subdivision. Such subdivision techniques are known.] The distance of these surfaces to the camera can then be determined, i.e., because the depths of the facial regions are measured with reference to the camera aperture.

Additional details of the above-referenced processes are now described. More particularly, the following description, including the pseudo code referenced below, provides exemplary steps for creating, from facial landmarks, a polygonal structure for a face.

Facial landmarks are read from the output of facial landmark detection software, such as that previously referenced. FIG. 1 shows numbered input vertices. The number associated with each vertex shall be called its index. Face region polygons are defined by index. For example, indices 1 . . . 65 in FIG. 1 are used. A zero-based count is employed, so indices in the code range from 0 . . . 64, inclusive, in this example. Additional vertices are used to build polygons. These additional vertices are synthesized using weighted interpolation and extrapolation:

synthLinearPoint interpolates a new vertex using a weight and two input vertices.

synthTriPoint extrapolates a new vertex using the perpendicular normal of two points, the centroid of two points, and a weight to place the new vertex.

synthQuadPoint extrapolates a new vertex using the perpendicular normal of two points, the location of a third point, and a weight to place the new vertex.

Each new vertex is synthesized 65 . . . 92 using the pseudo code synthUVs( ).

A winged-edge model is created by traversing gFaceRegionsRegions in order. An exemplary winged-edge model is illustrated with reference to FIG. 5. A method for creating this model is known and described, e.g., "Winged Edge Polyhedron Representation", Bruce G. Baumgart, Stanford University, Artificial Intelligence Project (1972), which is incorporated herein by reference.

Next, the winged-edge model is subdivided. An exemplary subdivision technique is known and described, e.g., "Subdivision Surfaces in Character Animation", Tony DeRose, Michael Kass, and Tien Truong. (SIGGRAPH '98), which is incorporated herein by reference.

Figure 7:
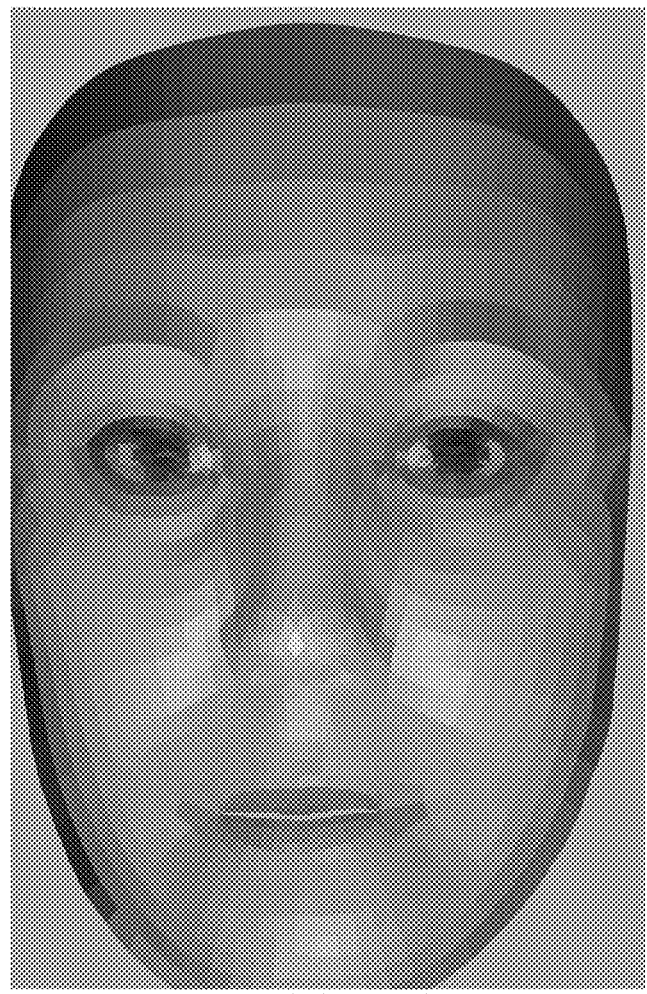

A 4×4 projection matrix for the camera is calculated using values that are known based on the type and model of the device being used. For each vertex in the subdivision surface: a corresponding point in the depth map is sampled; a scale correction for depth representation is applied; the z-depth value of vertex is set; and the vertex is un-projected using the inverse of the 4×4 projection matrix. For each polygon in the subdivision surface, color is sampled from the visible light photo image. An exemplary output of this process is shown in FIG. 7.

Below is representative of code that may be used to carry out the foregoing described processes.

The following provides the definition of face region polygons, where the first number is the vertex polygon count, followed by the numbered index of the Facial Landmark Vertex. Vertex indices over 65 are synthesized by weighted interpolation.

```
int32 gRightEyeRegion[] = {
    3, 16, 17, 64,
    3, 17, 18, 64,
    3, 18, 19, 64,
    3, 19, 20, 64,
    3, 20, 21, 64,
    3, 21, 22, 64,
    3, 22, 23, 64,
    3, 23, 16, 64,
    0
};
int32 gRightEyeTopRegion[] = {
    4, 4, 17, 16, 59,
    4, 4, 5, 18, 17,
    4, 5, 6, 19, 18,
    4, 6, 7, 20, 19,
    3, 7, 50, 20,
    0
};
int32 gRightCheekUpperRegion[] = {
    4, 16, 23, 66, 59,
    4, 23, 22, 68, 66,
    4, 22, 21, 67, 68,
    4, 21, 20, 50, 67,
    3, 50, 49, 67,
    0
};
```

```
int32 gRightCheekLowerRegion[] = {
  4, 66, 68, 72, 57,
  4, 68, 67, 71, 72,
  4, 67, 49, 48, 71,
  0
};
int32 gRightJawRegion[] =
{
  3, 29, 72, 71,
  3, 71, 75, 29,
  4, 71, 48, 47, 75,
  4, 30, 29, 75, 77,
  4, 77, 75, 47, 46,
  0
};
int32 gLeftEyeRegion[] = {
  3, 8, 9, 63,
  3, 9, 10, 63,
  3, 10, 11, 63,
  3, 11, 12, 63,
  3, 12, 13, 63,
  3, 13, 14, 63,
  3, 14, 15, 63,
  3, 15, 8, 63,
  0
};
int32 gLeftEyeTopRegion[] = {
  3, 8, 40, 0,
  4, 0, 1, 9, 8,
  4, 1, 2, 10, 9,
  4, 2, 3, 11, 10,
  4, 3, 51, 12, 11,
  0
};
int32 gLeftCheekUpperRegion[] = {
  4, 12, 51, 93, 13,
  4, 13, 93, 70, 14,
  4, 14, 70, 69, 15,
  4, 15, 69, 40, 8,
  3, 40, 69, 41,
  0
};
int32 gLeftCheekLowerRegion[] = {
  4, 41, 69, 73, 42,
  4, 69, 70, 74, 73,
  4, 70, 93, 53, 74,
  0
};
int32 gLeftJawRegion[] =
{
  3, 33, 76, 73,
  3, 73, 74, 33,
  4, 73, 76, 43, 42,
  4, 33, 32, 78, 76,
  4, 76, 78, 44, 43,
  0
};
int32 gForeheadRegion[] =
{
  4, 82, 86, 0, 40,
  4, 86, 88, 1, 0,
  4, 88, 84, 2, 1,
  4, 84, 90, 3, 2,
  4, 90, 80, 65, 3,
  4, 80, 89, 4, 65,
  4, 89, 83, 5, 4,
  4, 83, 87, 6, 5,
  4, 87, 85, 7, 6,
  4, 85, 81, 50, 7,
  0
};
int32 *gFaceRegionsRegion[] =
{
  gRightEyeRegion,
  gRightEyeTopRegion,
  gRightCheekUpperRegion,
  gRightCheekLowerRegion,
  gRightJawRegion,
  gLeftEyeRegion,
  gLeftEyeTopRegion,
  gLeftCheekUpperRegion,
  gLeftCheekLowerRegion,
  gLeftJawRegion,
  gForeheadRegion,
  gNoseBridgeRegion,
  gNoseRegion,
  gUpperMouthRegion,
  gUpperLipRegion,
  gLowerLipRegion,
  gChinRegion,
  NULL
};
char *gFaceRegionNames[] = {
  "RightEye",
  "RightEyeTop",
  "RightCheekUpper",
  "RightCheekLower",
  "RightJaw",
  "LeftEye",
  "LeftEyeTop",
  "LeftCheekUpper",
  "LeftCheekLower",
  "LeftJaw",
  "Forehead",
  "NoseBridge",
  "Nose",
  "UpperMouth",
  "UpperLip",
  "LowerLip",
  "Chin"
};
```

The following calculates a fourth vertex from three vertices and a weight:

```
Vec2f synthQuadPoint(int32 dex0, int32 dex1, int32 dex2, real32 scale)
{
  Vec2f diff = uvs[dex2] − uvs[dex0];
  Vec2f perpDiff(diff.y, −diff.x);
  perpDiff *= scale;
  Vec2f result = uvs[dex1] + perpDiff;
  return(result);
}
```

The following calculates a third vertex from two vertices and a weight:

```
Vec2f synthTriPoint(int32 dex0, int32 dex1, real32 t, real32 scale)
{
  Vec2f diff = uvs[dex1] − uvs[dex0];
  Vec2f perpDiff(diff.y, −diff.x);
  Vec2f midPoint = (diff*t) + uvs[dex0];
  perpDiff *= scale;
  Vec2f result = midPoint + perpDiff;
  return(result);
}
```

The following interpolates a vertex from two vertices and a weight:

```
Vec2f synthLinearPoint(int32 dex0, int32 dex1, real32 scale)
{
  Vec2f result = ((uvs[dex1] − uvs[dex0]) * scale) + uvs[dex0];
  return(result);
}
```

The following synthesizes all additional vertices from original landmark vertices:

```
void synthUVs(real32 foreheadScale)
{
  if (uvs.size() == 65)
  {
    uvs.resize(95);
    uvs[65] = synthLinearPoint(3, 4, 0.5f); // mid brow
    uvs[66] = synthQuadPoint(57, 58, 59, 0.2f); // right nose-cheek
    uvs[93] = synthQuadPoint(51, 52, 53, 0.2f); // left nose-cheek
    uvs[94] = synthLinearPoint(62, 61, 0.50f);
    uvs[67] = synthLinearPoint(49, 66, 0.30f); // right cheek0
    uvs[68] = synthLinearPoint(49, 66, 0.65f); // right cheek1
    uvs[69] = synthLinearPoint(41, 93, 0.30f); // left cheek0
    uvs[70] = synthLinearPoint(41, 93, 0.65f); // left cheek1
    uvs[71] = synthLinearPoint(48, 57, 0.35f); // right lower cheek0
    uvs[72] = synthLinearPoint(48, 57, 0.7f); // right lower cheek1
    uvs[73] = synthLinearPoint(42, 53, 0.35f); // left lower cheek0
    uvs[74] = synthLinearPoint(42, 53, 0.7f); // left lower cheek1
    uvs[75] = synthLinearPoint(47, 29, 0.5f); // right jaw
    uvs[76] = synthLinearPoint(43, 33, 0.5f); // left jaw
    uvs[77] = synthLinearPoint(46, 30, 0.45f); // right chin
    uvs[78] = synthLinearPoint(44, 32, 0.45f); // left chin
    uvs[79] = synthLinearPoint(45, 31, 0.6f); // mid chin
    uvs[80] = synthLinearPoint(45, 60, 1.0f + foreheadScale);
    // top forehead
    Vec2f rightHeadWidth = uvs [50] – uvs [60];
    Vec2f leftHeadWidth = uvs [40] – uvs [60];
    Vec2f templeMid =
      synthLinearPoint(60, 80, 0.6f);
    uvs[81] = templeMid + rightHeadWidth; // right temple
    uvs[82] = templeMid + leftHeadWidth; // left temple
    uvs[83] = synthTriPoint(80, 81, 0.45 f, -0.15f); // right mid arc
    uvs[84] = synthTriPoint(80, 82, 0.45 f, 0.15f); // left mid arc
    uvs[85] = synthTriPoint(81, 83, 0.45 f, 0.10f); // fill right
    uvs[86] = synthTriPoint(82, 84, 0.45 f, -0.10f); // fill left
    uvs[87] = synthTriPoint(85, 83, 0.5 f, 0.10f); // fill right
    uvs[88] = synthTriPoint(86, 84, 0.5 f, -0.10f); // fill left
    uvs[89] = synthTriPoint(80, 83, 0.50 f, -0.01f); // fill right
    uvs[90] = synthTriPoint(84, 80, 0.50 f, -0.01f); // fill left
    uvs[91] = synthQuadPoint(55, 56, 57, 0.45f); // right nostril
    uvs[92] = synthQuadPoint(53, 54, 55, 0.45f); // left nostril
  }
}
```

The aggregated data collected in the foregoing described manner is referred to herein as filtered data. Using the filtered data, it is possible to solve for a lighting model.

Methodologies for solving for the lighting model are now described. The exposure of the sensor/camera can be characterized by reading embedded data in the image stream, or by setting the exposure settings for the front camera or cameras on the hand-held device as previously described. The physical relationship of the sensor, the illuminant and the surface(s) to be measured can be determined, as previously described. The illuminant can be controlled by coupling the optical display to use as controlled lighting, as previously described. Using this information, it is possible to approximate the lighting model of the scene as viewed by the camera. The general problem of solving a lighting model to find the reflectance, color and surface characteristics of found geometry from a known scene with additional lighting and geometry data is known as inverse rendering. The more that is known about a specific scene, the more accurate the derived lighting model, and measured surface characteristics of the found geometry. Inverse rendering is a known technique and described in more detail in Patow and Pueyo, "*A Survey of Inverse Rendering Problems*", Computer Graphics Forum, P 663-687, V 22, N 4, https://doi.org/10.1111/j.1467-8659.2003.00716.x (2003), which is hereby incorporated by reference.

In one embodiment, the primary source of illumination is known, and the orientation and key planes of the face are found by sampling color from a color image captured from the selfie scan. The result of this sampling may be seen in FIG. 7. An inverse rendering technique may be used to solve for the reflectance and color characteristics of one or more planes of the face shown in FIG. 7. In one embodiment, an optimized inverse rendering technique used for solving these characteristics is described in Boivin and Gagalowicz, "*Inverse Rendering from a Single Image*", Dynamic Graphics Project, University of Toronto, Canada, Mirages Project, INRIA-Rocquencourt, France, www.dgp.toronto.edu/~boivin/pubs/cgiv2002.pdf (2002), which is hereby incorporated by reference.

A given technique is chosen to solve for the reflectance and color characteristics based on how well it matches the specific set of knowns and unknowns that are present in the problem to be solved. There are two main classes of Inverse Rendering; one is 'Direct Solving' which could be used if the ambient light is low or there are few unknowns or 'Indirect Solving' which could be used if there are more unknowns, e.g., more ambient light.

The Inverse Rendering technique uses an existing image, found geometry and dominant lighting to guess at initial values for the surface reflectance. The algorithm then minimizes the error between the synthetic rendering and the captured image as it iterates through the most likely changes in surface reflectance parameters to reduce the error. As used herein, synthetic rendering refers to drawing something that does not exist using computer graphic techniques. It this context, there is a 3D model, the light and the camera characteristics are known, so we can synthesize what we think we should see, and compare it to what is actually there. Then, variables (like the color of the skin surface, the shininess of the skin etc.) can be changed until the rendering and the actual facial surface match. The model is being solved through iteration (e.g., using Newton's method). If there are more unknowns (such as additional light), those will need to be approximated as well, which makes the problem more difficult and complicated to solve. This technique yields results of sufficient accuracy to determine the color and surface characteristics of a discrete area of the face if the optical display of the hand-held device is the dominant light source, or where additional light sources may be corrected/accounted for by methods as described herein. For environments in which there is more ambient or direct light, additional processing may be needed to reduce error.

While an inverse rendering technique is used to determine surface reflectance in one exemplary embodiment, other techniques known in the art may be used.

For instance, in another embodiment, the color and reflectance characteristics of the complexion surfaces may be solved using a relative light transport model. The transport model is composed of a non-directed graph of the connections between surfaces found by the scan, the optical display's light area, and the camera or imaging device. Each node of the graph is a surface region, light region, or camera viewpoint. The arcs of the graph connect each node and contain the portion of the radiant transfer between each node. For simplicity, connecting arcs may be limited to surface nodes connecting to adjoining surface nodes, the optical display and the camera. The relative changes of color and luminance of each surface are determined by their difference from a local mean of neighboring surface nodes. Each surface node in the transport graph is tagged with a location on the face. Local regions of the transport graph are graded on the amount of error they contain when compared to radiometric calculations of physical light transfer of the known graph. Regions with low error are compared with similarly tagged pre-determined relative transport graphs from example complexions. Contributions of known complexions are solved using a support vector machine.

In a further alternate embodiment, the surface reflectance of surfaces from the captured image may be solved using a global illumination model. The global illumination model supposes that most regions of the face are illuminated by the same lighting model, and so it is possible to generalize that model and reduce complexity. In one approach, the recorded scan color of each surface of the face is mapped onto a sphere. The mapping is performed by using the orientation of the surface patch or plane to find a matching orientation on the sphere. In one embodiment, the color of each sphere region is aggregated using an average. In another embodiment, it is collected and sorted to calculate a component median. The position of the sphere is determined by a weighted average of each contributing surface based on convexity. The diameter of the sphere is determined by the weighted extents of the contributing surfaces. The region of the sphere with the highest specular light is determined by comparing the known position of the optical display, the known position of the camera, and the angle and position of each region of the sphere, the found region being where the incident light angle matches the incident view angle relative to that region's surface. The region of the sphere with the highest diffuse light is found, that region being the one whose surface most fully faces the light of the optical display. An initial value for the diffuse reflectance, the specular reflectance, and ambient reflectance may be solved using an illumination model (e.g., the Phong Illumination model as known and described, Bui Tuong Phong, "*Illumination for Computer Generated Pictures*", Communications of ACM 18 (1975), no. 6, 311-317, which is hereby incorporated by reference). A model reflectance value for each region of the sphere is calculated. Each region of the sphere is graded based on the distance from the modeled color. Regions of the sphere past an error threshold may be marked for use in modeling environment lighting. Regions of the sphere within tolerance may be used to refine the predicted color and surface characteristics/reflectance of the user's complexion.

Additional details of the global illumination model are now described. In one such embodiment, data related to the lighting and surface of the target captured using the device/camera may be found by iteratively approximating this lighting and surface data using a rendering technique that employs a series of functions implemented as code running on a digital computer. The set of functions and their flow is referred to herein as the GlobalLightingModel. Inputs (InputData) to the GlobalLightingModel include the following:

The digital image of the user captured using the camera/device (referred to herein as ImageMap) in the form of a 2-dimensional array of pixels encoded as Red, Green, and Blue values in the color space known as sRGB.

The captured depth image associated with the captured digital image (referred to herein as DepthMap) in the form of a 2-dimensional array of depth values. These values are linear representations of the distance of the camera to the corresponding pixel in the ImageMap.

The winged-edge polygon model as described herein.

The exposure settings used in connection with the capture of the digital image of the user (i.e., ISO, shutter speed, and aperture).

The position of the camera aperture relative to the center of the illuminating portion of the display (referred to herein as PositionData).

The size of the illumination portion of the display (referred to herein as IlluminationData).

The calibrated light characteristics of the illuminating portion of the display for the model of the device used to capture the image.

The response curve of the CCD for the camera/device used to capture the ImageMap, adjusted for the model of the device, to provide SI units (referred to herein as ImageLightCurve). The curve is represented as a 0 . . . 0x0001000 array of discrete values, to provide a direct look-up for a 16-bit pixel value.

The ImageToCamera transform, which is the 4×4 transform matrix that converts a depth map x,y,depth pixel into an x, y, z vector with the camera aperture point as 0, 0, 0.

The LightToCamera transform, which is the 4×4 transform matrix that converts a Display Illuminant pixel UV into an x, y, z vector with the Camera aperture point as 0, 0, 0.

The LightSI, a constant SI illuminant value for the model of the device. Intermediate data is constructed for use in iteratively approximating the lighting and surface data in the ImageMap associated with the captured digital image.

The intermediate data to represent the 3-dimensional surface characteristics of the InputData is called the SurfaceMap. The SurfaceMap is constructed using a series of steps, including the following in one embodiment. The ImageMap and the DepthMap are resampled and combined to form a 2-dimensional array of a structure containing values for Red, Green, Blue, Depth, and Mask, referred to herein as the SurfaceMap. A MedianFilter is applied to the DepthMap to remove noise. A size is determined for the SurfaceMap, which typically will be 2× in width and height of the DepthMap dimensions. The SurfaceMap is allocated. The DepthMap is scaled using bicubic interpolation to fit the SurfaceMap. The depth component of the SurfaceMap is set to the DepthMap values. The ImageMap is transformed from sRGB to linear RGB, and the linear RGB is transformed by look-up using the ImageLightCurve to SI units. A Gaussian filter is applied to the SurfaceMap using the inverse of the scaling factor*1.5 as the theta for the Gaussian function. The ImageMap is scaled using Point Sampling to fit the SurfaceMap. The Red, Green and Blue components of the SurfaceMap are set to the ImageMap values. All the Mask components of the SurfaceMap are set to zero. The polygons in the model that represent the surfaces to be approximated are tagged. Because the model is built from Facial Feature Detection, these polygons will be the same for all instances of the Input Data. The tagged polygons in the model are rendered into the Mask component of the SurfaceMap so that mask area is set to a value of one.

The intermediate data to represent the 3-dimensional surface characteristics of the SurfaceMap as a GlobalLightingModel is referred to herein as the SphereMap. The SphereMap is constructed using a series of steps including the following, in one embodiment. The SurfaceMap is resampled and combined to form a 2-dimensional array of SphereMapValue structures containing values for Red, Green, Blue, Depth, and Accum. This is referred to herein as the SphereMap. A size is determined for the SphereMap. This is typically a square with a power of two for the width and height. It is chosen to be small enough to provide enough angular resolution for the model, and not so large that there are few samples from the input SurfaceMap. In an exemplary embodiment, the size is 256×256. The SphereMap is allocated. For each pixel in the SurfaceMap:

```
If (SurfaceMap [thisPixel] ].Mask = 1)
  A triangle with 3d vertices is built using neighboring pixels.
    Vertex0 is this pixel.
    Vertex1 is the pixel of the column to the right.
    Vertex2 is the pixel of column to the right and the row to the
      bottom.
  The triangle vertices are transformed to Camera space.
    Vertex0 = ImageToCamera * Vertex0...
  The normal of the triangle is found.
  The normal is scaled to 128.0.
  The normal is offset by 128, 128.
  U,V indicies are set, U = N.x, V = N.y
  For the U,V pixel in the SphereMap:
    SphereMap [V][U].Red += SurfaceMap [thisPixel]].Red
    SphereMap [V][U].Green += SurfaceMap [thisPixel]].Green
    SphereMap [V][U].Blue += SurfaceMap [thisPixel]].Blue
    SphereMap [V][U].Depth += SurfaceMap [thisPixel]].Depth
    SphereMap [V][U].Accum += 1
For each pixel in SphereMap:
  If (SphereMap [thisPixel].Accum > 0)
    SphereMap [V][U].Red /= SphereMap [V][U].Accum
    SphereMap [V][U].Green /= SphereMap [V][U].Accum
    SphereMap [V][U].Blue /= SphereMap [V][U].Accum
    SphereMap [V][U].Depth /= SphereMap [V][U].Accum
    SphereMap [V][U].Accum /= SphereMap [V][U].Accum
```

The intermediate data to represent the location of the screen area in the camera space is called the LightMap. The LightMap is constructed using steps including the following, in one embodiment. The LightMap is a 2-dimensional array of 3D vertices. The height and width of the LightMap have the same aspect ratio as the display illuminant of the device model used to capture the ImageMap. The height and width of the LightMap are calculated such that:

LightMap Width=((DisplayWidth in MM)+2.5)/5;

LightMap Height=((DisplayHeioght in MM)+2.5)/5;

The LightMap is allocated. The LightMap pixels are set:

LightMap[$V$][$U$].xyz=($V$,$U$)*LightToCamera.

The data output from the GlobalLightingModel (Output Data) include:

SynthSphereMap—a 2-dimensional array of a structure containing values for Red, Green, Blue as SI units CIELAB SurfaceColor—set to the average value of those pixels in the SphereMap that are 16 pixels in distance from SphereMap UV {128, 128}
  SpecularGamma=1.8
  SpecularScale=0.23
  ErrorTerm=Infinity
  MaxIteration=1000
  MinError=0.02

In one exemplary embodiment, the functions employed by the rendering technique described herein include the following:

```
GetSpherePixelNormal(REAL u, REAL v) ->{a, b, c}
{
  a = (u -128) / 128
  b = (v -128) / 128
  c = sqrt(1.0 - (a*a + b*b))
  return( {a, b, c})
}
RGBsiToCIELAB(RGB rgb) ->{lab}
{
  return(XYXtoLAB(LinRGBtoXYX(SiToLinRGB(rgb))))
}
CIELABtoRGBsi(RGB rgb) ->{lab}
{
  return(LinRGBToRGBsi(XYZ(ToLinRGB(LABToXYZ(rgb))))
}
BlinnPhong(SphereMapValue v, SI light, RGBsi rgb ) ->{rgb}
{
  toLight = light - v.xyz;
  d = length(toLight)
  lightNomal = normalize(toLight)
  surfaceNormal = GetSpherePixelNormal(v.uv)
  halfVector = normalize(surfaceNormal + lightNomal )
  falloff = 1.0/(d*d)
  specular = dot(halfVector, {0, 0, 1})
  specular = pow(specular, SpecularGamma)
  specular = specular * SpecularScale
  specular = specular * falloff
  diffuse = dot(lightNomal, surfaceNormal) * falloff
  return((rgb * diffuse) + (specular * LightColor))
}
AdjustSpecular(SpecularAmount, AccumRGBError) -> SpecularAmount
{
  error = average(AccumRGBError)
  SpecularAmount += error * 0.1
  return(SpecularAmount)
}
```

The iteration loop for generating the Output Data is referred to herein as solving for the lighting model. It is bound by the state of ErrorTerm and MaxIteration, as follows:

```
1. testRGB = CIELABtoRGBsi(SurfaceColor)
2. While (MaxIteration > 0 and ErrorTerm > MinError)
   a. Render SynthSphereMap
      i. For every pixel in SphereMap
         1. For every pixel in SphereMap
            a. If (SphereMap.accum > 0)
               i. For every pixel in LightMap
                  1. SynthSphereMap [currentPixel] =
                     BlinnPhong(SphereMap [currentPixel,
                     LightMap, testRGB)
   b. Compare SphereMap and SynthSphereMap
      i. RGBsi AccumRGBError = 0;
      ii. AccumCount = 0
      iii. For every pixel in SphereMap
         1. If (SphereMap.accum > 0)
            a. AccumCount++
            b. AccumRGBError += SphereMap [currentPixel].rgb-
               SynthSphereMap [currentPixel].rgb)
      iv. If AccumCount
         1. AccumRGBError = AccumRGBError/AccumCount
      v. Else
         1. Error, no data in SphereMap
   c. If (length(AccumRGBError) < ErrorTerm)
      i. ErrorTerm = length(AccumRGBError)
   d. MaxIteration--.
   e. testRGB = testRGB + (AccumRGBError * 0.1)
3. SurfaceColor = RGBsiToCIELAB(testRGB)
```

In this example, SpecularAmount is not affected but could be solved by adding additional iteration loops. For instance, step 1 could be replaced by saving SpecularGamma; steps 2.a . . . 2.d can be performed; and step 2.e replaced with SpecularAmount=AdjustSpecular(SpecularAmount, AccumRGBError).

In another embodiment, Ambient light may be filtered from the SphereMap by determining the average error between SphereMap and SynthSphereMap, and rejecting pixels that have an error that is greater than 2x the average error.

In another embodiment, Ambient light may be filtered from the SphereMap by comparing areas of the map across the lateral hemisphere (i.e., u=128−30 with u=128+30). Bright pixels found during this comparison may be rejected.

The solved output of the inverse rendering, or other, technique is the surface color and reflectance of a plurality of facial regions. The color and reflectance may be structured as a CIELAB color and an amount of specular reflectance. CIELAB color and specular reflectance may be structured as a search key, and the search key may be used to find and solve for a mixture, or proportions of discrete topical agents that may be combined to produce a custom cosmetic, as disclosed in the Background Patents.

There are limits imposed by direct solving of the physical lighting model. For instance, the technique of Bovin and Gagalowicz works well when the number of variables to solve is relatively low. The number of unknowns introduced by additional light sources of unknown color to the illumination model presents challenges in solution time and solution resolution that are difficult to overcome. It is possible, however, to assemble a hybrid system that improves the performance of Bovin and Gagalowicz's technique by training a machine learning (ML) system as to which solution paths are most likely and using these to guide an inverse rendering technique. In one embodiment, the solution paths for an inverse rendering algorithm may be enhanced by training a Hidden Markov Model to choose specific state transitions.

Referring now more particularly to the use of a ML system, a ML model for output of the color and surface reflectance of a plurality of facial regions may be trained using the filtered data. In an exemplary embodiment, the ML system is divided into components that solve for intermediate representations of the user's complexion. One component may be trained to solve for CIELAB color of known regions of the face. Another component may be trained to solve for the surface reflectance caused by the sebum content of the upper layers of the epidermis. The output of these components may be used to produce a search key to derive a mix and produce a custom topical agent.

Describing this embodiment now in more detail, the training data may include filtered data captured using a plurality of hand-held device types, with a series of users having a plurality of complexion characteristics. Each unit of filtered data used to train the system may be labeled, associating it with a specific hand-held device, a specific user, and quantitative measures of each user's complexion. These measurements may include, but are not limited to: (1) color spectra of a variety of facial regions; (2) CIELAB color of a variety of facial regions; and (3) reflectance characteristics of a variety of facial regions.

In one embodiment, a data collection process is used to collect and organize data to train an ML system. This process includes a series of steps: 1. Reference Subject Casting Intake. 2. Reference Subject Cohort Identification. 3. Reference Subject Training Data Collection Session. 4. Training Data Analysis. 5. Training Data Structuring. 6. ML Training. 7. ML Verification.

Reference Subject Casting Intake seeks to reach and engage a wide variety of subjects with a wide variety of complexion types and characteristics. These types include, but are not limited to, a variety of complexion tone, from dark to light, a variety of complexion undertone, from warm to cool, a variety of sebum content, a variety in response to sunlight, and/or a variety of skin artifacts and local coloration. Subjects are interviewed, and spectrophotometer scans are taken of a variety of complexion regions, including, but not limited to, Wrist, Forehead, Cheek, Upper Jaw, Lower Jaw, Lower Neck, and Upper Chest regions. Hair and eye color are noted, as well as a measure or estimation of pore size and complexion sebum content. Photo micrographs of skin regions are taken. This initial data is structured and placed in a data store.

Reference Subject Cohort identification seeks to identify key individuals from the Reference Subject Casting that may represent a cohort or group of the reference subjects. Identification of cohorts can be initially performed by k-value clustering based on an n-dimensional vector composed of CIELAB color and Sebum content. Other components of the vector may include pore size, and frequency of skin artifacts, such as freckles or spots. The Cohort list may be further filtered by removing outliers based on statistical means.

Reference Subject Training Data Collection Session seeks to collect data in a form useful for developing a training set for an ML network. Excess data is collected for verification purposes. For training, it collects reference training data in the form of the type of scan data taken by the hand-held device and associated software means. Several of such scans may be taken on a variety of different devices. It collects complexion surface data associated with the hand-held device scan data. The complexion surface data will include CIELAB color of each complexion region to output by the ML system, as well as sebum level, location and type of small skin artifacts such as freckles, spots, and acne, eye color, hair color, location and type of larger complexion artifacts such as wrinkles, darks patches or circles, skin color or tone variations. This data may be collected by discrete scan, by photo micrograph, by high resolution photo, or by high resolution 3D scan, by way of example.

Training Data Structuring seeks to organize and structure data from the Reference Subject Training Data Collection Session into a form that may train the selected ML system. In one embodiment, this is done by initially processing the scan data from the hand-held device and associated software means. Each scan is converted into a Winged-Edge Model as described above. The Winged-Edge Model contains 3D positions of the surfaces relative to the camera and optical display illuminant. The model also contains a key set of 2D coordinates, which will be referred to as UV coordinates, that are consistent for every trained Winged-Edge Model (all similar in structure, forming a standard) for this training. The model also contains a CIELAB color accumulated from one or more images collected by the software on the hand-held device. A solved lighting model is associated with the Winded-Edge Model, and used to solve an initial approximation of the surface reflectance of each polytope in the Winged-Edge Model. After the inputs, the desired outputs for each polytope of the Winged-Edge model are added. This output includes but is not limited to, CIELAB data scan by spectrophotometer of that region, the sebum content of that region, the location and type of small skin artifacts, and the location and type of larger skin artifacts within that region. It also includes a series of image maps. These maps are keyed to the UV coordinates of the Winged-Edge Model. Each map contains a variety of labeled image regions describing small and large skin artifacts including, but not limited to freckles, dark spots, acne, skin discoloration, wrinkles and dark circles.

ML Training seeks to aid in developing a set of ML graphs and key coefficients, weights, or constants in these graphs to convert the input of the hand-held device scan data (i.e., after its conversion into a Winged-Edge Model containing a full set of the input data as described above) into output data composed of a Winged-Edge Model containing information for each polytope region containing a subset of the collected trained data output described above. In one embodiment, the ML system is implemented as a model in TensorFlow (http://www.tensorflow.org/). Through a graph network implemented in TensorFlow, the ML network weights, constants and coefficients are set during the training process to output an ordinal set of polytopes from the standardized Winged-Edge Model (each polytope with relative 3D data), filtered CIELAB color from the recorded image, estimated reflected CIELAB color from the solved lighting model, and an error metric for the solved surface reflectance.

ML verification seeks to verify or prove that the training of each ML network produced in ML Training provides an output within a specific tolerance. During this process, additional data collected during the Reference Subject Training Data Collection Session is used as input to the ML System. The output is checked against the gathered output data, and the tolerance of the system is found. If the system is within tolerance, the ML system may be packaged and deployed. If the system is out of tolerance, ML Training resumes, and modifications are made to the structure of the ML graph, and the graph is re-trained.

After initial training, the ML system may no longer receive training, in some embodiments, or the network may receive intermittent training using a variety of techniques known to one skilled in the art. After training, in some embodiments, the ML system may be validated using a separate set of known training data. The ML system may then be used in a service residing on a server (as described below with reference to FIG. 8B), or reside on the hand-held device, to process user data into an output of CIELAB data pertaining to a specific facial region.

In the described embodiments, each component of the ML system may be trained in this manner. In such embodiments, the CIELAB outputs and sebum level outputs of two separate ML networks may be connected as inputs to the ML system trained to output the formula of a specific product.

In another exemplary embodiment, the ML component may take CIELAB color, sebum content, and the characteristics of a cosmetic product, and solve for proportions of ingredients for a custom topical agent, or mix. This component would replace the method in one or more of the Background Patents that use a search key and solve for a mix.

The ML system may be composed of a further processing stage supplying inputs and training data to a distributed network of nodes with that are connected with inputs, outputs, and a training input. Each node has a weight or set of weights and has an associated non-linear function that may trigger a signal to its output. The layering of the nodes may have many levels. The training inputs may be constructed so that they allow the weights to be adjusted based on the input and output state. The nodes may be constructed in a manner called a Neural Network, or they may be constructed in a manner called a Markov Model. The inputs may directly be tied to data inputs, or the input connections may pass through additional logic before entering as inputs to the network so that the breadth of the network may be much larger than the discrete number of inputs, or some inputs may be limited in represented breadth. The breadth and depth of the network may be configured automatically based on output quality based on training results.

Once the ML system is trained, the system may be used to process user data gathered interactively on the handheld device into manufacturing instructions for a topical agent, which may be customized or otherwise selected for the end user. So, for example, the user may take a picture using a phone; the phone may include software that performs certain processing as described herein (e.g., 3D model fitting and data preprocessing); the phone may then transmit to the server the 3D model with points (both skin and other parts of the face, such as eyes and lips) and associated colors. The ML system running on the server then determines the lighting model and the complexion color for each area of the face (e.g., skin color, hair color, lip color), as in a map.

Figure 8A:
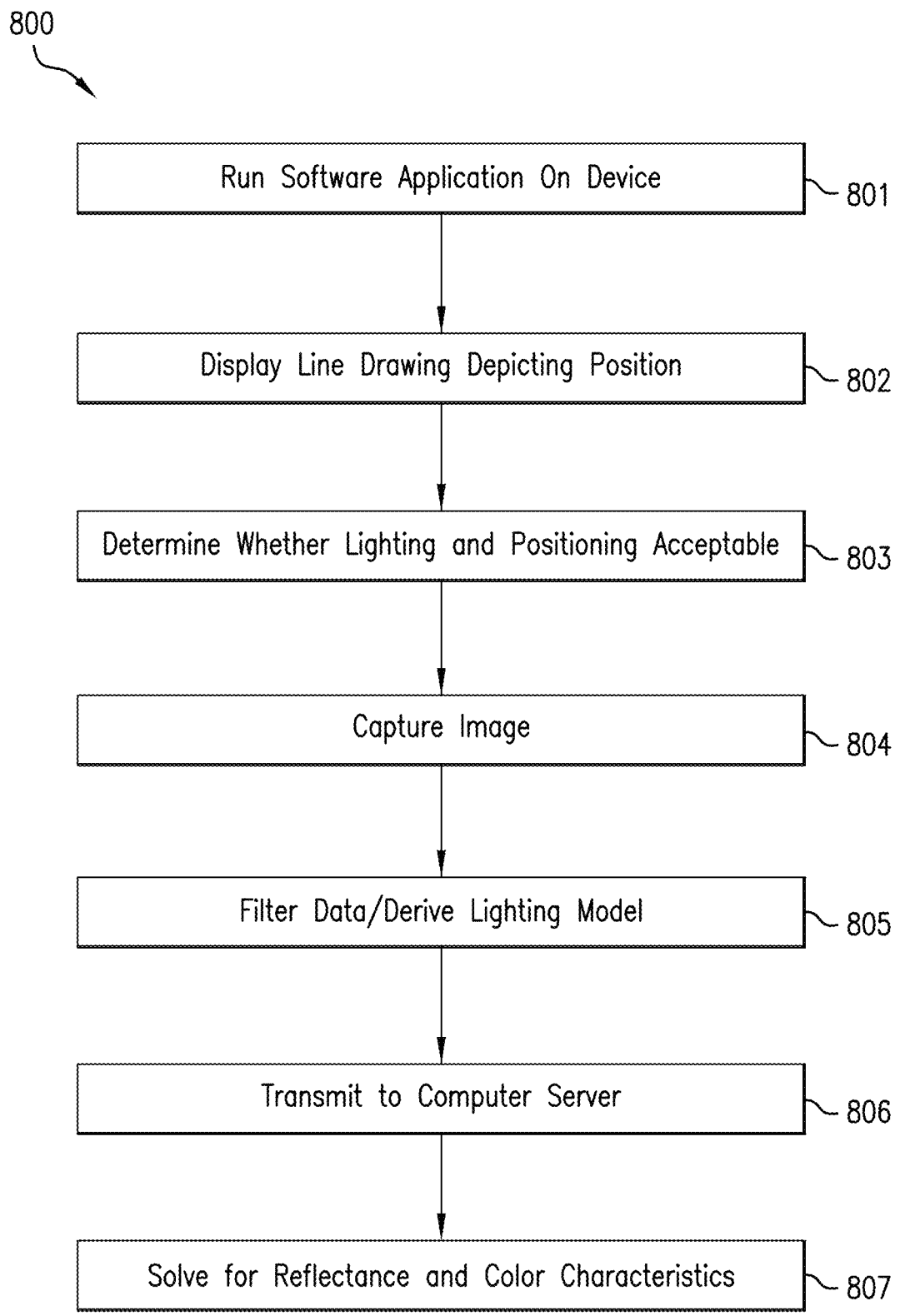
Figure 8B:
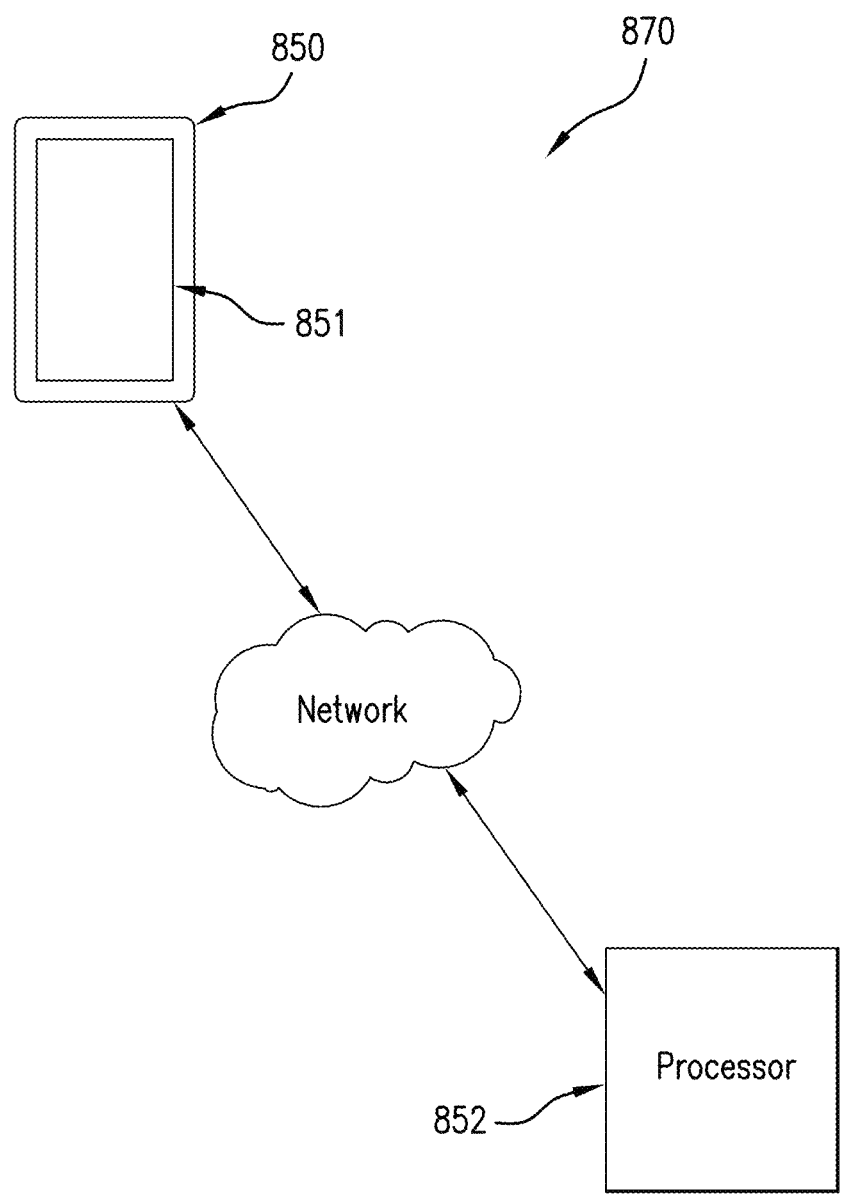

FIGS. 8A and 8B illustrate a method 800 and high-level system architecture 870, respectively, illustrating the steps and components associated with user activity and data flow in an exemplary embodiment. In step 801, the user runs a software application on her hand-held device 850.

In step 802, the application presents a display on the optical display 851 of hand-held device 850 showing a line drawing of the user depicting her position in real-time (e.g., as illustrated in FIG. 2). Here, the optical display 851 serves both as a continual source of illumination (e.g., in a darkened environment) and aids the user in proper positioning of her face in the optical display 851.

In step 803, the application determines whether the lighting of the environment and positioning of the user's face in acceptable for capturing a good quality image. In particular, the device may be programmed to detect an acceptable level of ambient or additional light, and to let the user know to move to a darker location. The exposure data stored in the image data stream may be compared with the exposure expected for illumination with the optical display, and an approximation of the amount of additional illumination calculated. The user interface/device may respond to the user that a given environment is suitable or unsuitable for the scan, the application may indicate that the user should move to a location with less light (e.g., as illustrated in FIG. 3) or that the room lighting is acceptable for scanning (e.g., as illustrated in FIG. 2) by changing the color of an indicator on the optical display 851, or some other indicator (visual, audible, or tactile).

By way of further example, the application may indicate that the user should move the hand-held device to center their image on the screen, and indicate this is complete by changing the display rendering (e.g., as illustrated in FIGS. 2 and 3, where FIG. 2 shows a display of the outline of the user's face and facial features with an illuminated line display and where FIG. 3 shows a circle, indicating that the positioning of the face is not optimal for taking a photo).

Upon depressing a button on the hand-held device 850, an image is captured, in step 804. That image may comprise a plurality of images (e.g., a single button press takes a plurality of images) and associated data, such as depth data, facial landmark data, and color image data. The data may be filtered and used to derive a lighting model, as described above, in step 805 (further illustrated and described in FIG. 8C), and transmitted to a computer server 852, in step 806. In step 807, the computer server 852 may use the lighting model and a processing technique, such as inverse rendering, to solve for the reflectance and color characteristics of one or more planes of the face.

Figure 8C:
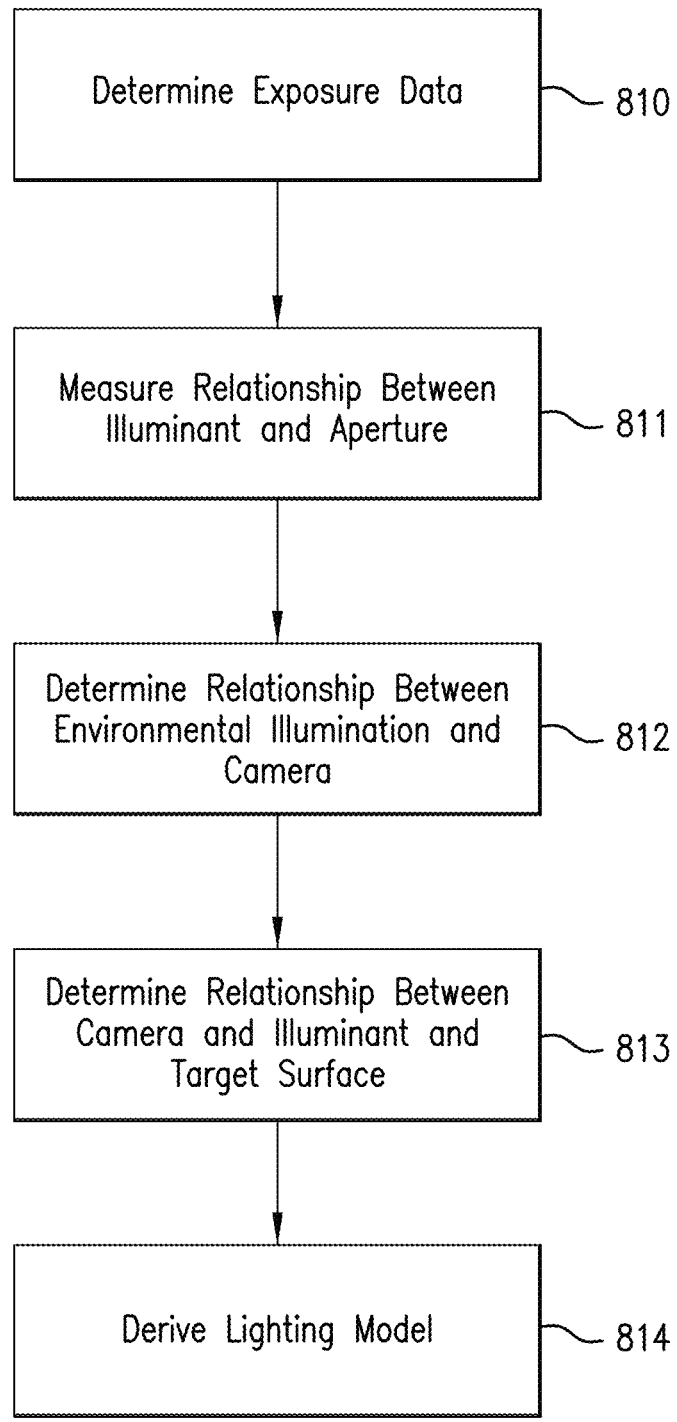

An exemplary method of obtaining filtered data (step 805) is now described with reference to FIG. 8C. It is specifically noted that the ordering of steps illustrated in this exemplary method is not limiting; in accordance with embodiments of the present invention, the steps may occur in an order different than that shown and described. In step 810, exposure data of the optical sensor in the hand-held device 850 is determined (e.g., from data embedded in the camera image data stream or set). In step 811, the relationship between the illuminant and the aperture of the sensor/camera in hand-held device 850 is measured. Such data, for a variety of different types of hand-held devices 850, may be determined and stored in or made available to server 852 for use in processing. In step 812, the relationship between environmental illuminants and the sensor/camera is determined. The techniques of obtaining proper illumination and positioning/alignment of the user, as described in steps 802 and 803 above, may be employed in order to determine the data reflecting this relationship. In step 813, the relationship between the sensor/camera and illuminant (determined in step 811) with the target surface is determined, wherein a 3D model of the target surface may be constructed in accordance with the techniques described previously. Using the data from steps 810, 811, 812 and 813, a lighting model of the scene as viewed by the camera can be determined (e.g., approximated or derived), in step 814.

In some embodiments, processing technique employed by the server 852 (step 807) may be enhanced using a ML system, as previously described. Intermediate results of the ML system may supply complexion data, which complexion data may be transmitted to the hand-held device 850 for viewing by the user.

After the steps described with reference to FIGS. 8A, 8B and 8C, the process may proceed in the manner described in one or more of the Background Patents, for ordering and manufacturing a topical agent (e.g., a customized or selected cosmetic product), for the user.

An exemplary embodiment involving alternative aspects of the present invention is now described. As in prior embodiments, the goal is to determine the skin tone ID of the end user using an image taken with the end user's hand-held device, e.g., mobile phone. The challenge is to account for the lighting environment in which the end user is present. Similar to other embodiments as described above, in this embodiment, the display screen of the device, e.g., a hand-held device or phone, may be used as a calibrated light source in a dark room environment, e.g., a low lighting environment, to take a selfie scan with the front facing camera as the capture device. The depth sensor incorporated into the device software for determining the depth of a body part to be detected for capturing an image, e.g., the depth of a face or facial region (facial depth sensor) may be used to provide a measurement of the distance from the screen of the device to the surface of the image target, e.g., the face. Using the known calibrated light source (the display screen), and the selfie scan data including the facial surface distance data, a facial complexion color (i.e., skin tone ID) can be computed.

A working example is now described. The end user is positioned in a dark-room environment with little or no ambient lighting, preferably as dark an environment as is available to the end user, such as a room with no windows, or having shades and/or curtains drawn, and with light sources such as lamps or computing device displays off. The end user opens an application previously downloaded onto a hand-held device, e.g., a mobile phone, and the application operates to open the camera on the mobile phone in the self-portrait mode (i.e., the "selfie-scan" mode). In a preferred embodiment, the application detects if the room is dark enough to proceed with the process and determine a skin tone ID of the user that is close enough to the actual skin tone ID within predetermined tolerances. If the room is not dark enough, the end user is signaled as such (using methods as described previously herein, or other methods known in the art) and the end user is directed to move to or create a darker environment. If the room is dark enough, the display of the hand-held device is illuminated with a white light, either automatically, or optionally by first providing an indication of a sufficiently dark lighting environment to the user (which is also described previously herein).

In an exemplary embodiment, the white light is in the shape of a rectangle that fills the entirety or near entirety of the hand-held device display screen. In some embodiments, the white light displays automatically upon the application detecting an adequately darkened room. A selfie-image of the end user is then captured with the camera on the hand-held device. This image is referred to herein as the Illuminance Image. The only light source from the hand-held device used to capture the Illuminance Image is the white light display. The Illuminance Image capture in the dark room environment, if dark enough, could be sufficient to estimate the skin tone ID of the end user.

However, practically, some ambient light will be present (e.g., from computer monitors, spaces at door bottoms or sides of window shades, etc.). In order to obtain the most accurate estimate of skin tone ID as possible, this ambient light should be accounted for. Thus, in the preferred embodiment, a second image of the end user is captured using the camera on the hand-held device. This second image—referred to as the Ambient Image—is captured with no illumination from the hand-held device and thus will include light only from ambient sources. As described more fully below, the light present in the Ambient Image may be removed from the Illuminance Image, thereby accounting for ambient light, leaving only known lighting conditions in the image of the end user. Based on these known lighting conditions, and other data points described more fully herein, the end user's skin tone ID may be more accurately predicted.

In a preferred embodiment, the Illuminance Image and the Ambient Images are taken in extremely close time proximity to each other to avoid movement of the end user between image captures.

Further details of exemplary embodiments are now described. As in other embodiments described above, software existing on the device/phone itself may be employed for certain functionality—e.g., obtaining a 3D image of the end user, which includes the distance from the target (e.g., the facial surface of the end user at various points) to the camera aperture of the device. In addition, other software may be in the form of an application, downloaded to the device/phone. Such downloaded software application may control the device display screen and camera setup, image captures, and/or data processing of image data, including but not limited to one or more of:

controlling set up of the device camera application programming interface (API), which controls the low-level settings of the camera, such as exposure settings, frame size, color and depth (3D data) settings, and which camera on the device is to be used (if two or more cameras are present);

controlling set up of the computer vision API setup, which provides a set of functions that take image data from the camera and return high-level data in return (e.g., taking data representing an image of a face and returning a list of 2D image points corresponding to specific facial features;

initializing a view for selfie scan display;

providing ambient light notifications (e.g., a notification that the environment is too bright for a selfie scan);

signaling to the user to adjust the capture scene for optimum data collection (e.g., instructing the user to adjust the distance between the capture object to the user);

controlling the image capture process (e.g., timing, display illumination, and exposure settings);

performing functions relating to the processing of image data; and storing error information and providing alerts.

In this exemplary embodiment, in a dark room environment, when the user opens the application, a line drawing of the user's face may be created and displayed, as described previously, enabling the user to properly align her face. However, in the present embodiment, instead of using a yellow illuminant as previously described, the image is shown with no illumination. As described previously, a series of images of the end user's face are captured. In a preferred embodiment, the captured images are High Dynamic Range (HDR) images. The HDR technique is generally known in the art, and uses standard methods to combine multiple images taken with different exposure settings into a single image with a high dynamic range, showing details much more clearly than non-HDR images. The HDR images are captured using a set of exposures of predetermined, calibrated values. The exposure settings used to create the HDR image described herein are unique, in that they are determined by calibration of a device model to represent the range of illumination provided by the device's display (Illuminance Image) and by ambient light (Ambient Image) encountered while in use.

Generally, an HDR image is collected by requesting a series of bracketed images using the programming interface provided by the operating system of the device/phone. Using such an interface, several images may be taken rapidly, one after the other, with different specified exposures. For instance, it is possible to request that a set of images be taken rapidly, one after another, that have the same shutter speed and aperture, but have different ISO settings. The ISO settings may be chosen to cover a wide range of illuminance. For instance, the first ISO setting may be chosen to provide the best exposure using the light from the device's display screen. The second ISO setting may be chosen to provide the best exposure for twice that illumination, i.e., where ambient light is equal to the light from the device's display. The third ISO setting may be chosen to provide the best exposure for illumination that is four times the first setting. This final exposure may be used to measure ambient light that is 3 times the illumination of the device's display. The response curve of the device's CCD for a single exposure (for example, the first setting) is such that illumination in excess of the device's display light is saturated and cannot be measured accurately. Examining the CCD response to the images with exposures as described above allows for the measurement of a greater amplitude of illumination.

To further understand this example, the disclosure herein refers to the "Luminance Image" and the "Ambient Image".

The Ambient Image is an image captured with the display illumination on the device set to black using exposure settings locked to predetermined, calibrated values. A series of three images may be taken to provide HDR, as described above. These may be recorded using the same series of exposure settings used in the Luminance Image.

The Luminance Image is an image captured with the display illumination on the device set to white using exposure settings set to automatic exposure, referred to herein as a primary scan. This provides a reference image that can adapt to a wide variety of lighting conditions. A series of images may be taken to provide HDR, as described above, and these may be recorded using the same series of exposure settings used in the Ambient Image. The depth data (i.e., the distance from the device sensor to the surface of the target) is recorded for the Luminance Image scan.

The exposure settings used for the Ambient and Luminence Images may be determined by calibrating a given device model. For instance, a given device model will have a known amount of light that is emitted when the screen is set to display a white field, and when the device is set to full brightness. That amount of light may be measured, and an exposure for the camera may be determined that best illuminates the complexion of the user at a common distance. The device OS allows the system/software application to determine which model of device is being used, and the calibration settings for that device model may be obtained from a data store, having been predetermined in the aforedescribed manner. An image with the display illumination on the device set to black, captured using exposure settings locked to predetermined calibrated values as just described, provides a reference image (Ambient Image) that shows only ambient light. Depth data (i.e., the distance from the device sensor to the surface of the target) is recorded for the Ambient Image scan.

A series of HDR images for ambient and luminance allows the software application to detect light over a greater range. In one embodiment, the Ambient and Luminance Images may be processed using the follow steps.

The three Ambient Images are combined into a single HDR image. This may be accomplished by correcting each image for the response curve of the CCD. Then, for each corresponding pixel of each image, the R, G, and B values are scaled by the exposure factor (e.g., 1× for the first, 2× for the second, and 3× for the third). These values are added together, and the result is stored with increased numerical resolution. For instance, if each input R, G, and B channel is represented by an unsigned 8 bit value, it may be stored as a 16 bit value.

The three Luminance Images are combined into a single HDR image as described in connection with the Ambient Image.

The HDR Ambient Image may be subtracted from the HDR Luminance Image, resulting in a "Corrected Luminance Image." This resulting Corrected Luminance Image accounts for the ambient light by removing it. In this embodiment, it is possible that the ambient light that has been removed is brighter than the light illuminating the subject's complexion from the display on the device. This is made possible by recoding each image using HDR imaging.

The data associated with the Corrected Luminance Image is stored in facial data format (e.g., structured and represented in a Winged-Edge Model, as referenced in detail above). The Winged-Edge Model contains a series of vertices, each vertex comprised of 2D points mapped to facial landmarks in the captured images and 3D points constructed also as previously described in detail above.

Each vertex is associated with a color. In one embodiment, the color of a vertex in the Winged-Edge Model may be found by the following steps.

As previously noted, the Winged-Edge Model may be subdivided into a finer structure. The model may be subdivided in this manner so that an average polygon in the model may represent an area of the subject's complexion that is approximate, e.g., a quarter of a square centimeter. Other scales of subdivision may be used within the scope of the present invention.

The color of the pixels in the Corrected Luminance Image is sampled for each polygon in the model. In one embodiment, this sampling is performed by inverse rendering. For example, for each pixel that may be rendered to describe the polygon, the R, G, B data for that pixel is accumulated as an average. This data is collected and stored at a higher resolution than the original pixel data. For instance, if the R, G, B data are represented as 16 bit unsigned integers, that data may be accumulated as 64 bit double precision floating point numbers and stored with each polygon in the model.

The R, G, and B color values for each vertex in the Winged-Edge Model may be determined by using the linkage in the Winged-Edge data structure to accumulate the color for each polygon that is linked to that vertex. The R, G, and B values may then be stored with each vertex in the model.

In some embodiments, the color resolution represented by the vertices in the model may be all that is needed. For instance, for the measurement of complexion color, the sampling of 0.5-centimeter patches may be sufficient. In other applications, such as determining the location of a specific skin artifact, such as a freckle, birthmark, or wrinkle, more resolution may be required, and select portions of the Corrected Luminance Image may be stored with the Winged-Edge Model.

As noted previously, because the Winged-Edged Model is assembled using facial landmarks, each vertex and polygon in the sub-divided model preserves a unique location in relationship to these facial landmarks. Additionally, because the same level of subdivision may be performed for each subject whose image is recorded, this will result in the same structural linkages (i.e., polygons to vertices and edges), as long as the facial landmarks are found. It is possible to know that a given polygon will always fall, for instance, on the tip of the nose, or in the middle of the left cheek. This allows each vertex associated with a color sample to be labeled by location. For instance, it is possible to label all of the vertices that comprise a specific region of the forehead so that they may be located. In this manner, it is possible to traverse the Winged-Edge Model and obtain color measurement for known complexion locations.

Accordingly, each vertex in the Winged-Edge Model may contain: a label indicating the portion of the face it represents; an RGB color accumulated from the Corrected Luminance Image; the Z depth obtained from the depth map of the device's 3D camera; the X, Y, Z position of the vertex relative to the hand-held device's camera viewpoint; and the A, B, C normal of the vertex relative to the hand-held device's camera viewpoint.

In addition to the data represented in the Winged-Edge Model, the system and method described herein may use pre-calculated data, such as calibration data. This is data that does not change from scan to scan, and represents physical properties of scanning devices; other constants, such as the range of reflectance of human skin; and constants for system operation. In some embodiments, these may include: the shutter timing for a specific model of a hand-held device, which may be used in specifying the series of exposures for HDR imaging as described above; the amount of acceptable signal to noise, as represented by the proportion of light emitted from the device's display for illumination to the amount of light detected in HDR Ambient Image; the absolute amount of light in metered units that is used as a threshold to trigger a state transition to and from Ambient Image capture; and the color response curve of the CCD for a specific model of a hand-held device.

The data comprising the Winged-Edge Model may be encoded for transmission. For example, GL Transmission Format (GLTF) may be used, which allows for the efficient transmission and loading of 3D images and models by applications by minimizing both the size of the asset and the runtime processing needed to unpack and use such assets.

The facial model data GLTF file may then be transmitted from the device/phone to a remote server or computing service using an encrypted transfer protocol (e.g., HTTPS) and stored in a repository. For example, an AWS S3, Amazon Web Services Simple Storage Services, repository may be used for this purpose. Use of this storage service provides a number of advantages. It allows transmission, e.g., of the facial model data, to and from the service to be encrypted. The service provides for storage of the facial model data to be sent from a hand-held device and supports a variety of operating systems used by hand-held devices. The service allows the facial model data to be accessed for further processing, and other transactions that result in the manufacture of custom cosmetic products and customer support. The service also allows for private intranet access in a secure manner.

Once transmitted to the computing service (e.g., remote cloud-based server), the facial model data is processed. The processing of the data may be implemented using a service, e.g., an AWS Lambda service, which allows the application to respond quickly to new information.

The flow for processing the facial model data is now described. In some embodiments, a preprocessing step may be used may involve color correction to account for the device itself (i.e., the screen and front facing camera). The type of device is identified from the image data and a correction is made for light and exposure (i.e., white point and color bias) associated with the specific device type (e.g., phone model).

In other embodiments, color correction accounting for the device type is incorporated while training the complexion color model (e.g., training data includes images taken with different device/model types and the machine learning engine takes into account differences during the training process) and, in such instances, a separate preprocessing step is not required.

Next, correction of color for each vertex is performed to account for depth data, e.g., the distance of the device display light to the surface of the image target (e.g., the face). Based on the 3D model of the image, a lighting equation is used to calculate distance falloff. Also removed is the lighting contribution based on angle falloff. More particularly, lighting on a surface becomes dimmer as it becomes more oblique to the light. To account for this, the 3D model and a lighting equation are used to calculate cosine falloff.

The following describes in more detail pre-processing/filtering of vertex data that may be used in some embodiments before such data is used as an input to the machine learning system:

1. Color may be corrected based on the response curve of the specific model of the hand-held device used for recording the image of the human subject. This will correct for the CCD response.

2. Cosine or angular falloff based on the orientation of vertex's surface normal relative to the device's display and the device's camera. Vertices that are turned in an oblique angle to the camera may be filtered or removed.

3. Amplitude fall-off of light based on the distance of the vertex from the device's display and the device's camera.

4. Color Correction of the vertex based on lighting, to removing ambient lighting.

The implementation of each of the foregoing processing steps may differ in accordance with alternate embodiments of this methodology. For instance, amplitude fall-off may be modeled as fall-off over distance from a point source, or as fall-off over distance from a surface representing the geometry of the device's display area. The basic order of the filtering is constant, however, because it is derived from the inverse of the transmission of information as light. In particular, light leaves the display, is reflected by an area of complexion represented by the vertex, and is received by the camera. Filtering is then performed with a correction for the camera, a correction for the orientation of the surface (including filtering for oblique angle), and a correction for the distance traveled back to the light. It may be appreciated that each filtering function may be combined and factored for simplicity or speed of operation, as any series of mathematical equation may be simplified for solving. In all embodiments, such filtering of data to account for the image capture process is performed before any use of the data as inputs to a machine learning engine.

In one embodiment, distance squared fall-off is used, according to the following equation:

$$FallCorrectedLum=Lum*(Magnitude(vertex.XYZ)2).$$

The inverse rendering equation for cosine fall-off may be applied. In one embodiment, point light at infinity fall-off is used, according to the following equation:

$$CosCorrectedLum=FallCorrectedLum*(1.0/Dot(vertex.ABC,light.Normal)).$$

Next, the data is processed using a machine learning engine, referred to herein as a complexion color model. The machine learning model must first be built and trained using data associated with human subjects. The data used to train the model may be obtained from a variety of sources, including: survey data, self-reported by human subject(s); reference photograph(s) of human subject(s), along with a color chart; skin color of human subject(s), measured by a spectrophotometer, in several regions of the subject's face (e.g., forehead, cheek (left and right), jaw (left and right), and décolletage), used as ground truth measurements; and facial image data obtained using the selfie-scan techniques described herein.

Cohorts of human subjects are selected in a manner best suited to fulfill the needs of the particular application. In one embodiment, the design of complexion data collection for training the machine learning system uses the following steps. A large cohort of human subjects is identified. This cohort may be discovered through use of an agency list, advertisement, or other method. The complexion characteristics of this large cohort is measured. This may be done using a reflection spectrophotometer. Readings may be taken for specific facial regions such as wrist, forehead, right and left cheeks, right and left jaw lines, and décolletage. The following data may be stored and may include, for example, for each subject: the human subject's name; the spectrophotometer data, which may be converted and stored as CIELAB data; data may be stored for the wrist, forehead, right and left cheeks, right and left jaw lines, and décolletage; and region data may be combined using a component median operation into a single CIELAB color and stored as the subject's complexion color. The large cohort data may be processed into a testing cohort. This may be done to improve sampling of color, for simplicity of testing, and for operational efficiency. In one embodiment, the large cohort is processed using k-value clustering. The clustering may be performed so that the center of each cluster is 3.0 DeltaE 2000 from others.

The quality and quantity of the training dataset greatly affects the performance of the resulting model.

Using this data, the model is built and trained, e.g., a tensor flow model as described in paragraph above.

The training of the model is now described in more detail. In one embodiment, an LCD display panel with a known luminance is used to calibrate ambient light for generating some of the training data for the machine learning model. Such data may be collected in the following manner. Each human subject records a series of selfie scans using a pre-determined set of instructions. The scans—three in the exemplary embodiment—are recorded with different amounts of known ambient light. The amounts of ambient light are known through use of the following technique. An LCD display panel with known luminance is placed two meters from the human subject for these sessions. Computer software causes the LCD display panel to display a series of .PNG images that attenuate the light emitted by the LCD display. Each .PNG image covers the entire display when it is shown. The .PNG image is a flat one-color image. That is, each pixel in the image has the same value. The .PNG image is an 8-bit RGB encoded image. The 8 bit image appears black when R,G,B={0, 0, 0}. The 8 bit image appears dark grey when R,G,B={80, 80, 80}. The 8 bit image appears medium grey when R,G,B={116, 116, 116}. The luminance emitted by the LCD display for each .PNG image is recorded at a distance of two meters. The subject takes three scans, each illuminated using a different .PNG image, thereby producing a known ambient light.

Generally, the training process uses the dataset (pairs of selfie scan data (GLTF) and ground truth measurements), to refine the weights to the complexion color model. For each facial region (i.e., forehead, left cheek, left lower jaw, décolletage, right lower jaw, and right cheek, each represented by a set of vertices), using the set's corrected vertex color (referenced above) as input, weights for patches within the facial regions are trained using Spectrophotometer CIELAB Ground Truth data. Curve fitting weights for each skin region are trained.

Continuing on with the description of the process for building and training the machine learning model, inputs for the model are determined. In this embodiment, specific labeled vertices of the Winged-Edge Model are used as input. The RGB values of each vertex are transformed to CIE l*a*b color space. An input channel is built of all vertices with a specific label. Outputs for the model are determined based on application needs and training data. For example, an output channel may be specified as a single CIE l*a*b color that will represent a complexion color for a facial region. A training input channel is specified as a single CIE l*a*b color that will be gathered using spectrophotometer scans of facial regions. The model design may take the form of a neural network model. Reducing relatively large vector inputs to smaller vector outputs are well-suited to specific forms of neural networks. Platforms exist to run models of this type reliably, and to scale them to serve large production systems. The depth and connectivity of the model is determined based on the complexity of the inputs. The model is trained using a wide variety of scan inputs. Random training data is withheld for testing. The model is evaluated using the test data. Filter, depth and connectivity changes are tested and optimized. A second stage of machine learning may be applied to the output of the first stage, described below. The end application may require that a single color be supplied that may be used to formulate a cosmetic that provides a unifying color for a user's complexion. In one embodiment, that color may be calculated by taking the component median of the region color outputs from the first stage of machine learning.

In other embodiments, it may be desirable to train a second stage of machine learning to supply a single cosmetic color suggestion. The training data for this may be a component median of the training inputs for the first stage, or it may be a unifying color specified by a Cosmetic Artist. In one embodiment, a second stage machine learning network is built and trained in the following manner. Inputs for the model are determined. In this embodiment, the CIE l*a*b color outputs for each facial region supplied by the first stage of machine learning are used. The input consists of a CIE l*a*b color and a facial region label, or input position. A large vector input is composed of these. Outputs for the model are determined based on application needs and training data. A single CIE l*a*b color specifying a unifying color for a facial cosmetic is output. The training data is a filtered set of recommendations by a Cosmetic Artist. Smoothing may be applied to a succession of similar training inputs. Component median filtering may be applied to a succession of similar training inputs. Cosmetic Artist training inputs may be combined with spectrophotometer scans based on additional artist input. A neural network model may be employed, as emulating artistic choice is a known use of neural networks. Platforms exist to run models of this type reliably, and to scale them to serve large production systems. The depth and connectivity of the model may be based on previous network models designed for aesthetic choice. The model is trained using a wide variety of scan inputs. For instance, selecting a distributed cluster of human subjects from a large cohort that represents a geographical region provides a broad variety of complexion types. Collecting input data from a Cosmetic Artist aesthetic color choices for several sessions, at different times, and preferably with similar, but different human subject groupings will provide a larger dataset and will result in capturing the Cosmetic Artist's intent more accurately than a smaller set. Selecting a hand-held device model, and then collecting data using many of these devices, rather than just a single device to provide a better sampling for that model's illumination and exposure characteristics.

In one embodiment, determining a single cosmetic color from a set of facial location color matches may be embodied in the following steps. A series of tests are performed on a sample set of human subjects with a variety of complexion types as described above. For each subject, a scan is taken. The component median of the CIELAB colors of each facial region is calculated as CIELAB input. The formula for a cosmetic is found using the CIELAB input and methods disclosed in in other patents, such as the Background Patents, owned by the present applicant. The formula is produced and applied to the subject by a Cosmetic Artist. The Cosmetic Artist approves the match or suggests a color correction. If approved, the measured color and the approved color are recorded and stored. If not approved, the color correction is applied to the CIELAB color and the test repeats. Curve fitting is performed on the difference between the measured color and the approved color based on CIELAB L* component. If a function is found that matches the Cosmetic Artist's intent, that function may be used to adjust the component median of the CIELAB colors of each facial region. In some cases, this function may provide, in some portions of the curve in L* mapping, a bias toward slightly lighter L* values, a reduction in A* values, and a slight increase in B* values. If the aesthetic choices have no apparent fit using a curve fit, a machine learning system may be built based on the CIELAB colors for each facial region as input, and the Cosmetic Artist's approved colors as training data.

An alternative embodiment to the component median approach to approximate the CIELAB color of the skin tone of the individual is the composite approach. When using the above-noted approach based on the component median, generally, each of the multiple facial regions (such the preferred regions of forehead, left cheek, left lower jaw, decolletage, right lower jaw and right cheek) outputs a single CIELAB color per region. Then, the median value of each of the CIE l*, a* and b* channels are used to output a single l*, a* and b* channel value to represent the total face using the median calculation per channel. This median calculation value is then used to represent the skin tone of the user as an estimate compared to the ground truth. In one approach, this data was obtained from a spectrophotometer.

Alternatively, in the composite approach, a linear weighting is sought across multiple regions, such as the six preferred regions noted above, to better match the ground truth. The composite approach allows for more depth in determining which of the six regions provides a better representation of the single CIELAB value to best match the skin tone representation of the ground truth. This is done by restricting the weightings, i.e., constraining the weights to sum to one, thus producing a method by which that allows for direct observation of which region(s) contribute the most and the least to the final output. By using the multiple regions and the composite approach, with the CIELAB vectors of each of the facial regions as the input and the ground truth color CIELAB single vector (from a spectrophotometer, for example) as the output, across the dataset of human models, the linear weightings can be calculated from multivariate linear regression with regularization.

To calculate the weights for each of the skin regions (for example, using the six preferred regions noted above), multivariate linear regression may be used. In addition, to ensure the weightings sum to one, θ regularization using the normal equation can be implemented. This is given by:

$$\theta = (XX + \lambda \cdot L)^{-1} X^T_y.$$

For example, where m is the number of sample inputs to outputs (x6 L*a*b* values of the region and the output spectrophotometer) and n is the number of skin regions (in this example, 6), then $$X = \begin{bmatrix} (x^{(1)})^T \\ \vdots \\ (x^{(m)})^T \end{bmatrix}$$

with X being the m×(n+1) matrix of the m sample colors for the n skin regions of CIELAB, and $$y = \begin{bmatrix} y^{(1)} \\ \vdots \\ y^{(m)} \end{bmatrix}$$

y=the m×1 matrix of output CIELAB colors for each of the respective samples.

θ is the weighting values (i.e., the linear weights that show the influence of each of the six regions, where 0 implies no influence and 1 implies total influence, where the values range from [0, 1].

λ is the regularization parameter, and $$L = \begin{bmatrix} 0 & 0 & \cdots & 0 \\ 0 & 1 & \cdots & 0 \\ \vdots & \vdots & \ddots & \vdots \\ 0 & 0 & \cdots & 1 \end{bmatrix}$$

Using the example regions noted above, and in practice, the decolletage region expressed far higher weighting levels than the other regions resulting in a greater accuracy in aligning with the ground truth color. This result also aligns with intuition and observations of the Cosmetic Artists in that this region is typically used by Cosmetic Artist's as a primary basis of color in their assessment of skin tone.

In addition, the composite approach may be used to adapt the weightings based on other outside factors that determine skin tone, such as the seasonal variation. If the dataset was captured during the winter season and another during the summer, there may be subtle yet critical differences in the weights to properly identify the skin tone of the user. An additional data source then that could feed the model may likely be sun exposure based on the individual's geography, outdoor lifestyle, etc.

The training data for the data set may need to be smoothed by applying a Gaussian filter to the difference of the component median, or the composite approach result, of the CIELAB colors of each facial region and the Cosmetic Artist's approved colors. For example using the component median, the smoothed delta is added to the component median, and this is used as training input. This process may be represented as follows:
1. The training data is smoothed and filtered:
   a. Let ListA be the Cosmetic Artist's approved colors.
   b. Let ListM be the component median of the CIELAB colors of each facial region.
   c. Let ListT be the training data result.
      i. ListT=Gaussian(ListA−ListM)+ListM
2. The ML system is trained using the filtered data.
3. The ML system results are verified.
   a. A test may be conducted where the Cosmetic Artist checks the recommendation made by the ML system.

Once built and trained, the complexion color model may be deployed as an AWS EC2 instance or hosted using other widely available services. The compute instance may operate synchronously or asynchronously. The compute instance provides an API interface to execute the complexion color model. The machine learning system may be implemented using a widely available machine learning platform, and the machine learning model may be represented as a data description that the machine learning platform uses to build and run the machine learning model. Code running on the compute instance:
1. Receives a request to process a user scan into a color recommendation through the API.
2. Loads a specific subject's facial model data (e.g., a GLTF file).
3. Loads and manages the machine learning model as needed.
4. Applies device color corrections to Winged-Edge vertices.
5. Applies inverse rendering corrections to Winged-Edge vertices.
6. Transforms Winged-Edge vertices into machine learning inputs.
7. Runs the machine learning model.
8. Returns the machine learning output data for the request.

In sum, the service is used to evaluate facial model data (e.g., a GLTF file) to predict (through inference) a complexion color in CIE L*a*b space. The captured image data (i.e., the facial model data in a GLTF file) is comprised of light from the device display and measured skin color. With a known light source (device display) and captured image, the model solves for the skin color, as described previously in more detail.

While certain exemplary embodiments described herein reference a topical agent comprising an agent applied to the skin such as a skin foundation, embodiments of the present invention are equally applicable to topical agents for other areas of the face, such as eye or lip, and/or for determining color that allows for matching or selection of agents to be applied to other areas, such as hair.

Some or all of the described functionality can be implemented in software and/or hardware on a user device. A user device can include, but is not limited to, smart phones, smart watches, smart glasses, tablet computers, portable computers, televisions, gaming devices, music players, mobile telephones, virtual reality goggles, laptops, palmtops, smart or dumb terminals, network computers, personal digital assistants, home assistants (such as Alexa™ or Google® Home™), which preferably have camera, wireless devices, information appliances, workstations, minicomputers, mainframe computers, or other computing devices, that is operated as a general purpose computer or a special purpose hardware device that can execute the functionality described herein. The software, for example, can be implemented on a general purpose computing device in the form of a computer including a processing unit, a system memory, and a system bus that couples various system components including the system memory to the processing unit.

Additionally or alternatively, some or all of the functionality can be performed remotely, in the cloud, or via software-as-a-service. For example, matching functions can be performed on one or more remote servers or other devices as described above that communicate with the user devices. The remote functionality can execute on server class computers that have sufficient memory, data storage, and processing power and that run a server class operating system (e.g., Oracle® Solaris®, GNU/Linux®, and the Microsoft® Windows® family of operating systems).

The systems can include a plurality of software processing modules stored in a memory and executed on a processor. By way of illustration, the program modules can be in the form of one or more suitable programming languages, which are converted to machine language or object code to allow the processor or processors to execute the instructions. The software can be in the form of a standalone application, implemented in a suitable programming language or framework.

Method steps of the techniques described herein can be performed by one or more programmable processors executing one or more computer programs to perform functions by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors. Generally, a processor will receive instructions and data from a read-only memory or a random access memory or both. The essential elements of a computer are a processor for executing instructions and one or more memory devices for storing instructions and data. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. One or more memories can store media assets (e.g., audio, video, graphics, interface elements, and/or other media files), configuration files, and/or instructions that, when executed by a processor, form the modules, engines, and other components described herein and perform the functionality associated with the components. The processor and the memory can be supplemented by or incorporated in special purpose logic circuitry.

In various implementations, a user device includes a web browser, native application, or both, that facilitates execution of the functionality described herein. A web browser allows the device to request a web page or other downloadable program, applet, or document (e.g., from the server(s)) with a web page request. One example of a web page is a data file that includes computer executable or interpretable information, graphics, sound, text, and/or video, that can be displayed, executed, played, processed, streamed, and/or stored and that can contain links, or pointers, to other web pages. In one implementation, a user of the device manually requests a web page from the server. Alternatively, the device automatically makes requests with the web browser. Examples of commercially available web browser software include Google® Chrome®, Microsoft® Internet Explorer®, Mozilla® Firefox®, and Apple® Safari®.

In some implementations, the user devices include client software. The client software provides functionality to the device that provides for the implementation and execution of the features described herein. The client software can be implemented in various forms, for example, it can be in the form of a native application, web page, widget, and/or Java, JavaScript, .Net, Silverlight, Flash, and/or other applet or plug-in that is downloaded to the device and runs in conjunction with the web browser. The client software and the web browser can be part of a single client-server interface; for example, the client software can be implemented as a plug-in to the web browser or to another framework or operating system. Other suitable client software architecture, including but not limited to widget frameworks and applet technology can also be employed with the client software.

A communications network can connect the devices with one or more servers and/or with each other. The communication can take place over media such as standard telephone lines, LAN or WAN links (e.g., T1, T3, 56 kb, X.25), broadband connections (ISDN, Frame Relay, ATM), wireless links (802.11 (Wi-Fi), Bluetooth, GSM, CDMA, etc.), for example. Other communication media are possible. The network can carry TCP/IP protocol communications, and HTTP/HTTPS requests made by a web browser, and the connection between the clients and servers can be communicated over such TCP/IP networks. Other communication protocols are possible.

The system can also be practiced in distributed computing environments where tasks are performed by remote processing devices that are linked through a communications network. In a distributed computing environment, program modules can be located in both local and remote computer storage media including memory storage devices. Other types of system hardware and software than that described herein can also be used, depending on the capacity of the device and the amount of required data processing capability. The system can also be implemented on one or more virtual machines executing virtualized operating systems such as those mentioned above, and that operate on one or more computers having hardware such as that described herein.

In some cases, relational or other structured databases can provide such functionality, for example, as a database management system which stores data for processing. Examples of databases include the MySQL Database Server or ORACLE Database Server offered by ORACLE Corp. of Redwood Shores, Calif., the PostgreSQL Database Server by the PostgreSQL Global Development Group of Berkeley, Calif., or the DB2 Database Server offered by IBM.

It should also be noted that implementations of the systems and methods can be provided as one or more computer-readable programs embodied on or in one or more articles of manufacture. The program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method comprising:
    displaying an image of a body portion of a user on an optical display of a device employed by the user, wherein the device comprises an image sensor and the image of the body portion of the user is sensed by the sensor;
    determining whether a position of the body portion image relative to the sensor is acceptable to allow for recording of the image of the body portion;
    determining whether a lighting environment associated with the sensor is acceptable to allow for recording of the image of the body portion;
    recording the image using the sensor to provide a recorded image having image data;
    processing the recorded image to determine lighting model data associated with the lighting environment; and
    determining reflectance and color characteristics associated with the body portion of the user based on the recorded image and the lighting model data.

2. The method of claim 1 wherein determining whether the position of the body portion relative to the sensor is acceptable for recording the image of the body portion comprises displaying a colored light on the optical display.

3. The method of claim 1 wherein determining whether the position of the body portion relative to the sensor is acceptable for recording the image of the body portion comprise displaying a lighted outline of the body portion on the optical display.

4. The method of claim 1 wherein determining whether the position of the body portion relative to the sensor is acceptable for recording the image of the body portion comprises actuating a tactile or an audible indicator on the device.

5. The method of claim 1 wherein determining whether that the lighting environment is acceptable for recording the image of the body portion comprises displaying a colored light on the optical display.

6. The method of claim 1 wherein determining that the lighting environment is acceptable for recording the image of the body portion comprises displaying a lighted outline of the body portion.

7. The method of claim 1 wherein determining that the lighting environment is acceptable for recording the image of the body portion comprises actuating a tactile or an audible indicator on the device.

8. The method of claim 1 wherein determining the lighting model comprises:
   measuring exposure data associated with the device;
   determining data describing a relationship between an illuminant on the device and an aperture of the image sensor;
   determining data describing a relationship between the lighting environment and the image sensor; and
   determining data describing a relationship between the image sensor, the illuminant and a surface of the body portion.

9. The method of claim 1 further comprising:
   determining a customized cosmetic formulation based in part on the reflectance and color characteristics.

10. The method of claim 1 wherein the optical display comprises an illuminant;
    wherein illumination of the body portion by the lighting environment is less than about 2% of the illumination provided by the illuminant; and wherein processing the recorded image to determine the lighting model data comprises direct computation.

11. The method of claim 1 wherein the optical display comprises an illuminant;
    wherein illumination of the body portion by the lighting environment is between about 2% and 10% of the illumination provided by the illuminant; and wherein processing the recorded image to determine the lighting model data comprises performing image filtering.

12. The method of claim 1 wherein the optical display comprises an illuminant;
    wherein illumination of the body portion by the lighting environment is between about 10% and 25% of the illumination provided by the illuminant; and wherein processing the recorded image to determine the lighting model data comprises performing a statistical estimate of bilateral symmetry.

13. The method of claim 1 wherein the optical display comprises an illuminant;
    wherein illumination of the body portion by the lighting environment is between about 25% and 40% of the illumination provided by the illuminant; and wherein processing the recorded image to determine the lighting model data comprises employing a machine learning technique.

14. The method of claim 1 wherein the optical display comprises an illuminant;
    and wherein when it is determined that the lighting environment associated with the sensor is not acceptable for recording the representation of the body portion, the method further comprises:
    instructing the user to modify the lighting environment so that the illumination of the body portion is less than about 2% of the illumination provided by the illuminant;
    illuminating the body portion with constant white light using the illuminant; and
    determining whether the illuminated body portion is positioned relative to the sensor to allow for recording of the image of the body portion by displaying on the optical display an outline of the body portion of the user to position the body portion within view of the sensor;
    wherein processing the recorded image to determine the lighting model data comprises direct computation.

15. A system comprising:
    one or more processors and non-transitory memory;
    machine-readable instructions stored in the memory that, upon execution by the one or more processors, cause the system to carry out operations comprising:
    displaying an image of a body portion of a user on an optical display of a device employed by the user, wherein the device comprises an image sensor and the image of the body portion of the user is sensed by the sensor;
    determining whether a position of the body portion image relative to the sensor is acceptable to allow for recording of the image of the body portion;
    determining whether a lighting environment associated with the sensor is acceptable to allow for recording of the image of the body portion;
    recording the image using the sensor to provide a recorded image having image data;
    processing the recorded image to determine lighting model data associated with the lighting environment; and
    determining reflectance and color characteristics associated with the body portion of the user based on the recorded image and the lighting model data.

* * * * *